US009526763B2

(12) United States Patent
Rohloff et al.

(10) Patent No.: US 9,526,763 B2
(45) Date of Patent: *Dec. 27, 2016

(54) SOLVENT/POLYMER SOLUTIONS AS SUSPENSION VEHICLES

(71) Applicant: Intarcia Therapeutics Inc., Boston, MA (US)

(72) Inventors: Catherine M. Rohloff, Los Altos, CA (US); Guohua Chen, Sunnyvale, CA (US); Andrew S. Luk, Castro Valley, CA (US); Rupal A. Ayer, Cupertino, CA (US); Paul R. Houston, Hayward, CA (US); Michael A. Desjardin, Aptos, CA (US); Pauline Zamora, Sausalito, CA (US); Stan Lam, Dublin, CA (US)

(73) Assignee: Intarcia Therapeutics Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,178

(22) Filed: Jun. 24, 2015

(65) Prior Publication Data
US 2015/0290291 A1 Oct. 15, 2015

Related U.S. Application Data

(60) Continuation of application No. 13/647,873, filed on Oct. 9, 2012, now Pat. No. 9,095,553, which is a
(Continued)

(51) Int. Cl.
*A61K 9/10* (2006.01)
*A61K 9/00* (2006.01)
(Continued)

(52) U.S. Cl.
CPC ............. *A61K 38/21* (2013.01); *A61K 9/0004* (2013.01); *A61K 9/0024* (2013.01); *A61K 9/10* (2013.01);
(Continued)

(58) Field of Classification Search
CPC .... A61K 38/21; A61K 38/043; A61K 38/085; A61K 38/09; A61K 38/105; A61K 38/11; A61K 38/1808; A61K 38/185; A61K 38/191; A61K 38/2242; A61K 38/225; A61K 38/24; A61K 38/26; A61K 38/27; A61K 38/28; A61K 38/31; A61K 9/0004; A61K 9/0024; A61K 9/10; A61K 47/12; A61K 47/14; A61K 47/02; A61K 47/10; A61K 47/20; A61K 47/26; A61K 47/32

See application file for complete search history.

(56) References Cited

U.S. PATENT DOCUMENTS 2,110,208 A  3/1938  Eggert
2,168,437 A  8/1939  Buercklin
(Continued)

FOREIGN PATENT DOCUMENTS

EP  0079405  5/1983
EP  0254394  1/1988
(Continued)

OTHER PUBLICATIONS

International Search Report and Written Opinion for International Application No. PCT/US2004/010107, mailed Nov. 4, 2004.
(Continued)

*Primary Examiner* — Blessing M Fubara
(74) *Attorney, Agent, or Firm* — Cooley LLP

(57) ABSTRACT

A nonaqueous, single-phase vehicle that is capable of suspending an active agent. The nonaqueous, single-phase vehicle includes at least one solvent and at least one polymer and is formulated to exhibit phase separation upon contact with an aqueous environment. The at least one solvent may be selected from the group consisting of benzyl benzoate, decanol, ethyl hexyl lactate, and mixtures thereof and the at least one polymer may be selected from the group consisting
(Continued)

of a polyester, pyrrolidone, ester of an unsaturated alcohol, ether of an unsaturated alcohol, polyoxyethylenepolyoxypropylene block copolymer, and mixtures thereof. In one embodiment, the at least one solvent is benzyl benzoate and the at least one polymer is polyvinylpyrrolidone. A stable, nonaqueous suspension formulation that includes the nonaqueous, single-phase vehicle and an active agent, and a method of forming the same, are also disclosed.

20 Claims, 7 Drawing Sheets

Related U.S. Application Data division of application No. 13/526,375, filed on Jun. 18, 2012, now Pat. No. 8,440,226, which is a continuation of application No. 13/158,137, filed on Jun. 10, 2011, now Pat. No. 8,206,745, which is a continuation of application No. 11/347,562, filed on Feb. 3, 2006, now Pat. No. 8,114,437.

(60) Provisional application No. 60/650,225, filed on Feb. 3, 2005.

(51) Int. Cl.
  *A61K 47/32* (2006.01)
  *A61K 47/10* (2006.01)
  *A61K 38/21* (2006.01)
  *A61K 38/08* (2006.01)
  *A61K 38/04* (2006.01)
  *A61K 38/09* (2006.01)
  *A61K 38/10* (2006.01)
  *A61K 38/18* (2006.01)
  *A61K 38/11* (2006.01)
  *A61K 38/19* (2006.01)
  *A61K 38/22* (2006.01)
  *A61K 38/24* (2006.01)
  *A61K 38/26* (2006.01)
  *A61K 38/27* (2006.01)
  *A61K 38/28* (2006.01)
  *A61K 38/31* (2006.01)
  *A61K 38/35* (2006.01)
  *A61K 38/36* (2006.01)
  *A61K 47/12* (2006.01)
  *A61K 47/14* (2006.01)
  *A61K 47/02* (2006.01)
  *A61K 47/20* (2006.01)
  *A61K 47/26* (2006.01)

(52) U.S. Cl.
  CPC .......... *A61K 38/043* (2013.01); *A61K 38/085* (2013.01); *A61K 38/09* (2013.01); *A61K 38/105* (2013.01); *A61K 38/11* (2013.01); *A61K 38/185* (2013.01); *A61K 38/1808* (2013.01); *A61K 38/191* (2013.01); *A61K 38/225* (2013.01); *A61K 38/2242* (2013.01); *A61K 38/24* (2013.01); *A61K 38/26* (2013.01); *A61K 38/27* (2013.01); *A61K 38/28* (2013.01); *A61K 38/31* (2013.01); *A61K 38/35* (2013.01); *A61K 38/36* (2013.01); *A61K 47/02* (2013.01); *A61K 47/10* (2013.01); *A61K 47/12* (2013.01); *A61K 47/14* (2013.01); *A61K 47/20* (2013.01); *A61K 47/26* (2013.01); *A61K 47/32* (2013.01); *Y10T 29/494* (2015.01); *Y10T 29/49826* (2015.01)

(56) References Cited

U.S. PATENT DOCUMENTS

| | | |
|---|---|---|
| 3,025,991 A | 3/1962 | Gillon |
| 3,122,162 A | 2/1964 | Sands |
| 3,625,214 A | 12/1971 | Higuchi |
| 3,632,768 A | 1/1972 | Bergy et al. |
| 3,732,865 A | 5/1973 | Higuchi et al. |
| 3,797,492 A | 3/1974 | Place |
| 3,869,549 A | 3/1975 | Geller |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |
| 4,111,202 A | 9/1978 | Theeuwes |
| 4,211,771 A | 7/1980 | Witkowski et al. |
| 4,243,030 A | 1/1981 | Lynch et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher et al. |
| 4,439,196 A | 3/1984 | Higuchi |
| 4,455,143 A | 6/1984 | Theeuwes et al. |
| 4,455,145 A | 6/1984 | Theeuwes |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |
| 4,695,623 A | 9/1987 | Stabinsky |
| 4,727,138 A | 2/1988 | Goeddel et al. |
| 4,734,284 A | 3/1988 | Terada et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,820,638 A | 4/1989 | Swetly et al. |
| 4,826,144 A | 5/1989 | Balsells |
| 4,830,344 A | 5/1989 | Balsells |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,952,402 A | 8/1990 | Sparks et al. |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |

(56) References Cited

U.S. PATENT DOCUMENTS

| | | |
|---|---|---|
| 5,006,346 A | 4/1991 | Theeuwes et al. |
| 5,019,382 A | 5/1991 | Cummins, Jr. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,126,142 A | 6/1992 | Ayer et al. |
| 5,134,244 A | 7/1992 | Balsells |
| 5,137,727 A | 8/1992 | Eckenhoff |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,207,752 A | 5/1993 | Sorensen et al. |
| 5,209,746 A | 5/1993 | Balaban et al. |
| 5,213,809 A | 5/1993 | Wright et al. |
| 5,219,572 A | 6/1993 | Sivaramakrishnan |
| 5,221,278 A | 6/1993 | Linkwitz et al. |
| 5,223,265 A | 6/1993 | Wong |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| 5,278,151 A | 1/1994 | Korb et al. |
| 5,279,608 A | 1/1994 | Cherif Cheikh |
| 5,284,655 A | 2/1994 | Bogdansky et al. |
| 5,290,271 A | 3/1994 | Jernberg |
| 5,300,302 A | 4/1994 | Tachon et al. |
| 5,308,348 A | 5/1994 | Balaban et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magruder et al. |
| 5,324,280 A | 6/1994 | Wong et al. |
| 5,336,057 A | 8/1994 | Fukuda et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,429,602 A | 7/1995 | Hauser |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,543,156 A | 8/1996 | Roorda et al. |
| 5,545,618 A | 8/1996 | Buckley et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,633,011 A | 5/1997 | Dong et al. |
| 5,635,213 A | 6/1997 | Nystrom et al. |
| 5,639,477 A | 6/1997 | Maruyama et al. |
| 5,645,850 A | 7/1997 | Bezwada et al. |
| 5,648,088 A | 7/1997 | Bezwada et al. |
| 5,660,847 A | 8/1997 | Magruder et al. |
| 5,660,858 A | 8/1997 | Parikh et al. |
| 5,660,861 A | 8/1997 | Jao et al. |
| 5,668,170 A | 9/1997 | Gyory |
| 5,676,942 A | 10/1997 | Testa et al. |
| 5,686,097 A | 11/1997 | Taskovich et al. |
| 5,690,925 A | 11/1997 | Gray et al. |
| 5,690,952 A | 11/1997 | Magruder et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,711,967 A | 1/1998 | Juch |
| 5,713,847 A | 2/1998 | Howard, III et al. |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Hahn et al. |
| 5,782,396 A | 7/1998 | Mastri et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,874,388 A | 2/1999 | Hsu |
| 5,876,746 A | 3/1999 | Jona et al. |
| 5,882,676 A | 3/1999 | Lee et al. |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,928,666 A | 7/1999 | Farinas et al. |
| 5,932,547 A | 8/1999 | Stevenson et al. |
| 5,938,654 A | 8/1999 | Wong et al. |

(56) References Cited

U.S. PATENT DOCUMENTS

| | | |
|---|---|---|
| 5,939,286 A | 8/1999 | Johnson et al. |
| 5,942,223 A | 8/1999 | Bazer et al. |
| 5,948,430 A | 9/1999 | Zerbe et al. |
| 5,958,909 A | 9/1999 | Habener |
| 5,962,023 A | 10/1999 | Jamiolkowski et al. |
| 5,972,370 A | 10/1999 | Eckenhoff et al. |
| 5,972,373 A | 10/1999 | Yajima et al. |
| 5,976,109 A | 11/1999 | Heruth |
| 5,985,305 A | 11/1999 | Peery et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,029,361 A | 2/2000 | Newman |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,113,938 A | 9/2000 | Chen et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,191,102 B1 | 2/2001 | DiMarchi et al. |
| 6,204,022 B1 | 3/2001 | Johnson et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| 6,258,377 B1 | 7/2001 | New et al. |
| 6,261,584 B1 | 7/2001 | Peery et al. |
| 6,268,343 B1 | 7/2001 | Knudsen et al. |
| 6,270,787 B1 | 8/2001 | Ayer |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,924 B2 | 10/2002 | Knudsen et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 | 2/2003 | Peterson et al. |
| 6,528,486 B1 | 3/2003 | Larsen et al. |
| 6,541,021 B1 | 4/2003 | Johnson et al. |
| 6,544,252 B1 | 4/2003 | Theeuwes et al. |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,902,744 B1 | 6/2005 | Kolterman et al. |
| 6,903,186 B1 | 6/2005 | Dong |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,612,176 B2 | 11/2009 | Wright et al. |

(56) References Cited

U.S. PATENT DOCUMENTS

| | | | |
|---|---|---|---|
| 7,655,254 B2 * | 2/2010 | Dennis | A61K 9/0004 424/422 |
| 7,655,257 B2 | 2/2010 | Peery et al. | |
| 7,666,835 B2 | 2/2010 | Bloom et al. | |
| 7,682,356 B2 * | 3/2010 | Alessi | A61K 9/0004 604/222 |
| 7,727,519 B2 | 6/2010 | Moran | |
| 7,731,947 B2 | 6/2010 | Eliaz et al. | |
| 7,741,269 B2 | 6/2010 | Young et al. | |
| 7,825,091 B2 | 11/2010 | Bloom et al. | |
| 7,829,109 B2 | 11/2010 | Chen et al. | |
| 7,833,543 B2 | 11/2010 | Gilson et al. | |
| 7,879,028 B2 * | 2/2011 | Alessi | A61K 9/0004 604/222 |
| 7,919,109 B2 | 4/2011 | Berry et al. | |
| 7,959,938 B2 | 6/2011 | Rohloff et al. | |
| 7,964,183 B2 | 6/2011 | Eliaz et al. | |
| 8,048,438 B2 | 11/2011 | Berry et al. | |
| 8,052,996 B2 | 11/2011 | Lautenbach et al. | |
| 8,058,233 B2 | 11/2011 | Cowley et al. | |
| 8,101,576 B2 | 1/2012 | Bloom | |
| 8,114,430 B2 | 2/2012 | Rohloff et al. | |
| 8,114,437 B2 * | 2/2012 | Rohloff | A61K 9/0004 424/423 |
| 8,158,150 B2 | 4/2012 | Lautenbach et al. | |
| 8,173,150 B2 | 5/2012 | Berry et al. | |
| 8,206,745 B2 * | 6/2012 | Rohloff | A61K 9/0004 424/486 |
| 8,211,467 B2 | 7/2012 | Rohloff et al. | |
| 8,217,001 B2 | 7/2012 | Cowley et al. | |
| 8,257,691 B2 | 9/2012 | Eliaz et al. | |
| 8,263,736 B2 | 9/2012 | Bloom | |
| 8,268,341 B2 | 9/2012 | Berry | |
| 8,273,365 B2 | 9/2012 | Lautenbach et al. | |
| 8,273,713 B2 | 9/2012 | Pittner et al. | |
| 8,278,267 B2 | 10/2012 | Weyer et al. | |
| 8,298,561 B2 | 10/2012 | Alessi et al. | |
| 8,299,025 B2 | 10/2012 | Alessi et al. | |
| 8,343,140 B2 | 1/2013 | Alessi et al. | |
| 8,367,095 B2 | 2/2013 | Lautenbach et al. | |
| 8,372,424 B2 | 2/2013 | Berry et al. | |
| 8,398,967 B2 | 3/2013 | Eliaz et al. | |
| 8,440,226 B2 * | 5/2013 | Rohloff | A61K 9/0004 424/486 |
| 8,460,694 B2 | 6/2013 | Rohloff et al. | |
| 8,470,353 B2 | 6/2013 | Lautenbach et al. | |
| 8,801,700 B2 | 8/2014 | Alessi et al. | |
| 8,865,202 B2 | 10/2014 | Zerbe et al. | |
| 8,926,595 B2 | 1/2015 | Alessi et al. | |
| 8,940,316 B2 | 1/2015 | Alessi et al. | |
| 8,992,962 B2 | 3/2015 | Lautenbach et al. | |
| 9,095,553 B2 | 8/2015 | Rohloff et al. | |
| 2001/0012511 A1 | 8/2001 | Bezwada et al. | |
| 2001/0021377 A1 | 9/2001 | Jamiolkowski et al. | |
| 2001/0021822 A1 | 9/2001 | Ayer | |
| 2001/0022974 A1 | 9/2001 | Ayer | |
| 2001/0027311 A1 | 10/2001 | Chen et al. | |
| 2001/0031790 A1 | 10/2001 | Beisswenger | |
| 2001/0036472 A1 | 11/2001 | Wong et al. | |
| 2002/0001631 A1 | 1/2002 | Okumu | |
| 2002/0004481 A1 | 1/2002 | Cleland et al. | |
| 2002/0012818 A1 | 1/2002 | Ruppi et al. | |
| 2002/0034532 A1 | 3/2002 | Brodbeck et al. | |
| 2002/0037309 A1 | 3/2002 | Jaworowicz et al. | |
| 2002/0048600 A1 | 4/2002 | Bhatt et al. | |
| 2002/0136848 A1 | 9/2002 | Yoshii et al. | |
| 2002/0137666 A1 | 9/2002 | Beeley et al. | |
| 2002/0141985 A1 | 10/2002 | Pittner et al. | |
| 2002/0197185 A1 | 12/2002 | Jamiolkowski et al. | |
| 2002/0197235 A1 | 12/2002 | Moran | |
| 2003/0032947 A1 | 2/2003 | Harper et al. | |
| 2003/0044467 A1 | 3/2003 | Brodbeck et al. | |
| 2003/0045454 A1 | 3/2003 | Okumu et al. | |
| 2003/0059376 A1 | 3/2003 | Libbey, III et al. | |
| 2003/0060425 A1 | 3/2003 | Ahlem et al. | |
| 2003/0104063 A1 | 6/2003 | Babcock et al. | |
| 2003/0108609 A1 | 6/2003 | Berry et al. | |
| 2003/0113380 A1 | 6/2003 | Ramstack et al. | |
| 2003/0114837 A1 | 6/2003 | Peterson et al. | |
| 2003/0118660 A1 | 6/2003 | Rickey et al. | |
| 2003/0138403 A1 | 7/2003 | Drustrup | |
| 2003/0138491 A1 | 7/2003 | Tracy et al. | |
| 2003/0157178 A1 | 8/2003 | Chen et al. | |
| 2003/0170289 A1 | 9/2003 | Chen et al. | |
| 2003/0180364 A1 | 9/2003 | Chen et al. | |
| 2003/0186858 A1 | 10/2003 | Arentsen | |
| 2003/0211974 A1 | 11/2003 | Brodbeck et al. | |
| 2003/0215515 A1 | 11/2003 | Truong-Le et al. | |
| 2004/0001689 A1 | 1/2004 | Goldsmith et al. | |
| 2004/0001889 A1 | 1/2004 | Chen et al. | |
| 2004/0002442 A1 | 1/2004 | Pan et al. | |
| 2004/0022859 A1 | 2/2004 | Chen et al. | |
| 2004/0024068 A1 | 2/2004 | Levy et al. | |
| 2004/0024069 A1 | 2/2004 | Chen et al. | |
| 2004/0029784 A1 | 2/2004 | Hathaway | |
| 2004/0039376 A1 | 2/2004 | Peery et al. | |
| 2004/0097906 A1 | 5/2004 | Fereira et al. | |
| 2004/0101557 A1 | 5/2004 | Gibson et al. | |
| 2004/0102762 A1 | 5/2004 | Gilbert | |
| 2004/0115236 A1 | 6/2004 | Chan et al. | |
| 2004/0142867 A1 | 7/2004 | Oi et al. | |
| 2004/0142902 A1 | 7/2004 | Struijker-Boudier | |
| 2004/0151753 A1 | 8/2004 | Chen et al. | |
| 2004/0157951 A1 | 8/2004 | Wolf | |
| 2004/0198654 A1 | 10/2004 | Glaesner et al. | |
| 2004/0209801 A1 | 10/2004 | Brand et al. | |
| 2004/0224903 A1 | 11/2004 | Berry et al. | |
| 2004/0225113 A1 | 11/2004 | LaFleur et al. | |
| 2004/0243106 A1 | 12/2004 | Ayer | |
| 2004/0265273 A1 | 12/2004 | Li et al. | |
| 2004/0266683 A1 | 12/2004 | Hathaway et al. | |
| 2004/0266692 A1 | 12/2004 | Young et al. | |
| 2005/0004557 A1 | 1/2005 | Russell | |
| 2005/0008661 A1 | 1/2005 | Fereira et al. | |
| 2005/0009742 A1 | 1/2005 | Bertilsson et al. | |
| 2005/0010196 A1 | 1/2005 | Fereira et al. | |
| 2005/0070883 A1 | 3/2005 | Brown et al. | |
| 2005/0079200 A1 | 4/2005 | Rathenow et al. | |
| 2005/0079202 A1 | 4/2005 | Chen et al. | |
| 2005/0095284 A1 | 5/2005 | Trautman | |
| 2005/0101943 A1 | 5/2005 | Ayer et al. | |
| 2005/0106214 A1 | 5/2005 | Chen | |
| 2005/0112188 A1 | 5/2005 | Eliaz et al. | |
| 2005/0118206 A1 | 6/2005 | Luk et al. | |
| 2005/0118221 A1 | 6/2005 | Blakely et al. | |
| 2005/0131386 A1 | 6/2005 | Freeman et al. | |
| 2005/0131389 A1 | 6/2005 | Peterson et al. | |
| 2005/0175701 A1 | 8/2005 | Pan et al. | |
| 2005/0201980 A1 | 9/2005 | Moran | |
| 2005/0215475 A1 | 9/2005 | Ong et al. | |
| 2005/0266087 A1 | 12/2005 | Junnarkar et al. | |
| 2005/0271702 A1 | 12/2005 | Wright et al. | |
| 2005/0276856 A1 | 12/2005 | Fereira et al. | |
| 2005/0281879 A1 | 12/2005 | Chen et al. | |
| 2006/0013879 A9 | 1/2006 | Brodbeck et al. | |
| 2006/0014678 A1 | 1/2006 | Cowley et al. | |
| 2006/0030526 A1 | 2/2006 | Liu et al. | |
| 2006/0069029 A1 | 3/2006 | Kolterman et al. | |
| 2006/0084604 A1 | 4/2006 | Kitaura et al. | |
| 2006/0094652 A1 | 5/2006 | Levy et al. | |
| 2006/0141040 A1 | 6/2006 | Chen et al. | |
| 2006/0142234 A1 | 6/2006 | Chen et al. | |
| 2006/0160736 A1 | 7/2006 | Nadler | |
| 2006/0178304 A1 | 8/2006 | Juul-Mortensen et al. | |
| 2006/0193918 A1 | 8/2006 | Rohloff et al. | |
| 2006/0216242 A1 | 9/2006 | Rohloff et al. | |
| 2006/0233841 A1 | 10/2006 | Brodbeck et al. | |
| 2006/0246138 A1 | 11/2006 | Rohloff et al. | |
| 2006/0251618 A1 | 11/2006 | Dennis et al. | |
| 2006/0263433 A1 | 11/2006 | Ayer et al. | |
| 2006/0264890 A1 | 11/2006 | Moberg et al. | |
| 2006/0280795 A1 | 12/2006 | Penhasi et al. | |
| 2006/0293232 A1 | 12/2006 | Levy et al. | |

(56) References Cited

U.S. PATENT DOCUMENTS

| | | |
|---|---|---|
| 2007/0027105 A1 | 2/2007 | Junnarkar et al. |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0038316 A1 | 2/2008 | Wong et al. |
| 2008/0064636 A1 | 3/2008 | Bloom et al. |
| 2008/0091176 A1 | 4/2008 | Alessi et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0312157 A1 | 12/2008 | Levy et al. |
| 2009/0022727 A1 | 1/2009 | Houston et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0247463 A1 | 10/2009 | Wright et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2011/0076317 A1 | 3/2011 | Alessi et al. |
| 2011/0104111 A1 | 5/2011 | Rohloff et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0178687 A1 | 7/2012 | Alessi et al. |
| 2012/0208755 A1 | 8/2012 | Leung |
| 2013/0052237 A1 | 2/2013 | Eliaz et al. |
| 2015/0111818 A1 | 4/2015 | Alessi et al. |
| 2015/0231062 A1 | 8/2015 | Lautenback et al. |
| 2015/0231256 A1 | 8/2015 | Berry et al. |

FOREIGN PATENT DOCUMENTS

| | | |
|---|---|---|
| EP | 0295411 | 12/1988 |
| EP | 0368339 | 5/1990 |
| EP | 0373867 | 6/1990 |
| EP | 0431942 | 6/1991 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1600187 | 1/2009 |
| EP | 2020990 | 9/2010 |
| FR | 640907 | 7/1928 |
| GB | 1049104 | 11/1966 |
| GB | 1518683 | 7/1978 |
| JP | 9241153 | 9/1997 |
| JP | 11-100353 | 4/1999 |
| JP | 2006/213727 A | 8/2006 |
| NZ | 592113 | 8/2012 |
| TW | 200634060 | 10/2006 |
| WO | WO 91/07160 | 5/1991 |
| WO | WO 93/06819 | 4/1993 |
| WO | WO 93/06821 | 4/1993 |
| WO | WO 93/08832 | 5/1993 |
| WO | WO 93/09763 | 5/1993 |
| WO | WO 93/23083 | 11/1993 |
| WO | WO 94/09743 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |
| WO | WO 95/34285 | 12/1995 |
| WO | WO 9601134 | 1/1996 |
| WO | WO 96/03116 | 2/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO 97/15289 | 5/1997 |
| WO | WO 97/15296 | 5/1997 |
| WO | WO 97/28181 | 8/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/27962 | 7/1998 |
| WO | WO 98/27963 | 7/1998 |
| WO | WO 98/30231 | 7/1998 |
| WO | WO 98/32463 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/04768 | 2/1999 |
| WO | WO 99/16419 | 4/1999 |
| WO | WO 99/25728 | 5/1999 |
| WO | WO 99/29306 | 6/1999 |
| WO | WO 99/33446 | 7/1999 |
| WO | WO 99/33449 | 7/1999 |
| WO | WO 99/39700 | 8/1999 |
| WO | WO 99/40788 | 8/1999 |
| WO | WO 99/44659 | 9/1999 |
| WO | WO 99/62501 | 12/1999 |
| WO | WO 99/64061 | 12/1999 |
| WO | WO 00/13663 | 3/2000 |
| WO | WO 00/29206 | 5/2000 |
| WO | WO 00/38652 | 7/2000 |
| WO | WO 00/39280 | 7/2000 |
| WO | WO 00/40273 | 7/2000 |
| WO | WO 00/41548 | 7/2000 |
| WO | WO 00/45790 | 8/2000 |
| WO | WO 00/54745 | 9/2000 |
| WO | WO 00/66138 | 11/2000 |
| WO | WO 01/43528 | 6/2001 |
| WO | WO 01/51041 | 7/2001 |
| WO | WO 01/78683 | 10/2001 |
| WO | WO 02/28366 | 4/2002 |
| WO | WO 02/36072 | 5/2002 |
| WO | WO 02/43800 | 6/2002 |
| WO | WO 02/45752 | 6/2002 |
| WO | WO 02/47716 | 6/2002 |
| WO | WO 02/067895 | 9/2002 |
| WO | WO 02/069983 | 9/2002 |
| WO | WO 02/076344 | 10/2002 |
| WO | WO 02/085428 | 10/2002 |
| WO | WO 03/000230 | 1/2003 |
| WO | WO 03/011892 | 2/2003 |
| WO | WO 03/024357 | 3/2003 |
| WO | WO 03/024503 | 3/2003 |
| WO | WO 03/030923 | 4/2003 |
| WO | WO 03/041684 | 5/2003 |
| WO | WO 03/072113 | 9/2003 |
| WO | WO 03/072133 | 9/2003 |
| WO | WO 2004/002565 | 1/2004 |

(56) References Cited

FOREIGN PATENT DOCUMENTS

| WO | WO 2004/052336 | 6/2004 |
|---|---|---|
| WO | WO 2004/056338 | 7/2004 |
| WO | WO 2004/089335 | 10/2004 |
| WO | WO 2005/048930 | 6/2005 |
| WO | WO 2005/048952 | 6/2005 |
| WO | WO 2005/102293 | 11/2005 |
| WO | WO 2006/017772 | 2/2006 |
| WO | WO 2006/023526 | 3/2006 |
| WO | WO 2006/081279 | 8/2006 |
| WO | WO 2006/083761 | 8/2006 |
| WO | WO 2006/084139 | 8/2006 |
| WO | WO 2006/101815 | 9/2006 |
| WO | WO 2006/111169 | 10/2006 |
| WO | WO 2007/024700 | 3/2007 |
| WO | WO 2007/056681 | 5/2007 |
| WO | WO 2007/075534 | 7/2007 |
| WO | WO 2007/084460 | 7/2007 |
| WO | WO 2007/133778 | 11/2007 |
| WO | WO 2007/140416 | 12/2007 |
| WO | WO 2008/021133 | 2/2008 |
| WO | WO 2008/061355 | 5/2008 |
| WO | WO 2008/133908 | 11/2008 |
| WO | WO 2008/134425 | 11/2008 |
| WO | WO 2009/109927 | 9/2009 |

OTHER PUBLICATIONS

International Preliminary Report on Patentability for International Application No. PCT/US2004/010107, dated Feb. 24, 2005.
International Search Report and Written Opinion for International Application No. PCT/US2004/010106, mailed Aug. 30, 2004.
International Preliminary Report on Patentability for International Application No. PCT/US2004/010106, dated Jul. 8, 2005.
Office Action for U.S. Appl. No. 11/347,562, mailed Feb. 4, 2010, 9 pages.
Office Action for U.S. Appl. No. 11/347,562, mailed Sep. 7, 2010, 20 pages.
International Search Report and Written Opinion for International Application No. PCT/US2006/003192, mailed Jul. 28, 2006.
International Preliminary Report on Patentability for International Application No. PCT/US2006/003192, dated Aug. 7, 2007.
Office Action for U.S. Appl. No. 12/827,265, mailed Mar. 30, 2011, 10 pages.
Office Action for U.S. Appl. No. 13/158,137, mailed Dec. 13, 2011, 13 pages.
Office Action for U.S. Appl. No. 13/526,375, mailed Sep. 14, 2012, 13 pages.
Office Action for U.S. Appl. No. 12/925,864, mailed Dec. 13, 2011, 11 pages.
Office Action for U.S. Appl. No. 13/647,228, mailed Jan. 2, 2013, 5 pages.
Office Action for U.S. Appl. No. 13/647,873, mailed Sep. 11, 2014, 7 pages.
Office Action for U.S. Appl. No. 13/647,873, mailed Jan. 3, 2013, 5 pages.
Office Action for U.S. Appl. No. 13/647,873, mailed Jun. 18, 2013, 5 pages.
Office Action for U.S. Appl. No. 11/755,494, mailed Dec. 27, 2010, 10 pages.
Office Action for U.S. Appl. No. 11/755,494, mailed Jun. 8, 2011, 15 pages.
International Search Report and Written Opinion for International Application No. PCT/US2007/069990, mailed Feb. 26, 2008.
International Preliminary Report on Patentability for International Application No. PCT/US2007/069990, dated Dec. 3, 2008.
Office Action for U.S. Appl. No. 13/433,287, mailed Jun. 19, 2012, 5 pages.
Office Action for U.S. Appl. No. 13/601,939, mailed Oct. 25, 2012, 5 pages.
Office Action for U.S. Appl. No. 13/740,187, mailed Apr. 11, 2013, 6 pages.
Office Action for U.S. Appl. No. 13/898,358, mailed Jul. 17, 2014, 6 pages.
Office Action for U.S. Appl. No. 13/209,328, mailed Feb. 16, 2012, 5 pages.
International Search Report and Written Opinion for International Application No. PCT/US2004/009755, mailed Nov. 22, 2004.
International Preliminary Report on Patentability for International Application No. PCT/US2004/009755, dated Jul. 8, 2005.
Office Action for U.S. Appl. No. 12/148,896, mailed Aug. 23, 2012, 6 pages.
Office Action for U.S. Appl. No. 12/148,896, mailed Oct. 20, 2009, 10 pages.
Office Action for U.S. Appl. No. 12/148,896, mailed May 14, 2010, 8 pages.
International Preliminary Report on Patentability for International Application No. PCT/US2008/005235, mailed Apr. 11, 2008.
International Search Report and Written Opinion for International Application No. PCT/US2008/005235, mailed Dec. 19, 2008.
Office Action for U.S. Appl. No. 12/927,432, mailed Mar. 26, 2014, 8 pages.
Bell, G. I. et al., "Hamster preproglucagon contains the sequence of glucagon and two related peptides," Nature, 302:716-718 (1983).
Clark, J. B. et al., "The diabetic Zucker fatty rat," Proc. Soc. Exp. Biol., Med., 173(1): 68-75 (1983).
Henry, R. R. et al., "Comparing ITCA 650, continuous subcutaneous delivery of exenatide via DUROS® device, vs. twice daily exenatide injections in metformin-treated type 2 diabetes," ITCA 650 phase 2 oral presentation at the 46th Annual Meeting of the European Association for the Study of Diabetes in Stockholm, Sweden (Sep. 20-24, 2010).
Dash, A. K. et al., "Therapeutic applications of implantable drug delivery systems," Journal of Pharmacological and Toxicological Methods, 40(1):1-12 (1998).
Deacon, C. F. et al., "GLP-1-(9-36) amide reduces blood glucose in anesthetized pigs by a mechanism that does not involve insulin secretion," Am. J. Physiol. Endocrinol. Metab., 282:E873-E879 (2002).
Efendic, S. et al., et al., "Overview of incretin hormones," Horm. Metab. Res., 36(11-12):742-746 (2004).
Eissele, R. et al., "Rat gastric somatostatin and gastrin release: interactions of exendin-4 and truncated glucagon-like peptide-1 (GLP-1) amide," Life Sci., 55(8):629-634 (1994).
Eng, J. et al., "Purification and structure of exendin-3, a new pancreatic secretagogue isolated from Heloderma horridum venom," J. Biol. Chem., 265(33):20259-20262 (1990).
Eng, J. et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Ghiglione, M., et al., "How glucagon-like is glucagon-like peptide-1?" Diabetologia, 27:599-600 (1984).
Goke, R. et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gutniak, M. et al., "Antidiabetogenic effect of glucagon-like peptide-1 (7-36)amide in normal subjects and patients with diabetes mellitus," N. Engl. J. Med., 326(20):1316-1322 (1992).
Heinrich, G. et al., "Pre-proglucagon messenger ribonucleic acid: nucleotide and encoded amino acid sequences of the rat pancreatic complementary deoxyribonucleic acid," Endocrinol., 115:2176-2181 (1984).
Lopez, L. C. et al., "Mammalian pancreatic preproglucagon contains three glucagon-related peptides," Proc. Natl. Acad. Sci. USA, 80(18):5485-5489 (1983).
Lund, P. K. et al., "Pancreatic preproglucagon cDNA contains two glucagon-related coding sequences arranged in tandem," Proc. Natl. Acad. Sci. USA, 79(2):345-349 (1982).

(56) References Cited

OTHER PUBLICATIONS

Meier, J. J. et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Mojsov, S., "Structural requirements for biological activity of glucagon-like peptide-I," Int. J. Peptide Protein Research, 40:333-343 (1992).
Vrabec, J. T., "Tympanic membrane perforations in the diabetic rat: a model of impaired wound healing," Otolaryngol. Head Neck Surg., 118(3 Pt. 1):304-308 (1998).
Young, A. A. et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).
Nauck, M. A. et al., "Normalization of fasting glycaemia by intravenous GLP-1 ([7-36 amide] or [7-37]) in type 2 diabetic patients," Diabet. Med., 15(11):937-945(1998).
Patzelt, C. et al., "Identification and processing of proglucagon in pancreatic islets," Nature, 282:260-266 (1979).
Peterson, R. G. et al., "Zucker Diabetic Fatty Rat as a Model for Non-insulin-dependent Diabetes Mellitus," ILAR Journal, 32(3):16-19 (1990).
Peterson, R. G. et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pohl, M. et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J. Biol. Chem., 273(16):9778-9784 (1998).
Press Release, Intarcia Therapeutics, Inc., "Intarcia Presents Positive ITCA 650 Phase 2 Study Results for Type 2 Diabetes at EASD," (Sep. 22, 2010).
Press Release, "Intarcia Therapeutics Announces Final Results from a Phase 2 Study of Injectable Omega Interferon plus Ribavirin for the Treatment of Hepatits C Genotype-1," NLV Partners Press Coverage Portofolio News (Apr. 12, 2007).
Schepp, W. et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Sparks, J. D. et al., "Lipoprotein alterations in 10- and 20-week-old Zucker diabetic fatty rats: hyperinsulinemic versus insulinopenic hyperglycemia," Metabolism, 47(11):1315-1324 (1998).
Tseng, C. C. et al., "Glucose-dependent insulinotropic peptide: structure of the precursor and tissue-specific expression in rat," PNAS USA, 90(5):1992-1996 (1993).
Adolf, "Human interferon omega-a review," Mult. Sclr. 1:S44-47 (1995).
Costantino et al., "Protein Spray Freeze Drying. 2. Effect of Formulation Variables on particle Size and Stability," J. Pharm. Sci. 91:388-395 (2002).
Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).
Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).
Ishiwata et al., "Clinical effects of the recombinant feline interferon-omega on experimental parvovirus infection in beagle dogs," J. Vet. Med. Sci. 60(8):911-917 (1998).
Johnson et al., "How interferons fight disease," Sci. Am. 270(5):68-75 (May 1994).
Lublin et al., "Defining the clinical course of multiple sclerosis: results of an internatinal survey," Neurology. 46:907-911 (1996).
Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).
Nielsen, "Incretin mimetics and DPP-IV inhibitors for the treatment of type 2 diabetes," Drug Discovery Today 10(10):703-710 (May 15, 2005).
Palmeri et al., "5-Fluorouracil and recombinant α-interferon-2a in the treatment of advanced colorectal carcinoma: a dose optimization study," J. Chemotherapy 2(5):327-330 (Oct. 1990).
Patti et al., "Natural interferon-b treatment of relapsing-remitting and secondary-progressive multiple sclerosis patients: two-year study," Acta. Neurol. Scand. 100:283-289 (1990).
Paty et al., "Interferon beta-1 b is effective in relapsing-remitting multple sclerosis," Neurology 43:662-667 (1993).
PCT International Search Report for PCT/US2009/000916, 4 pages (Aug. 12, 2009).
Quianzon et al., "Lixisenatide—Once-daily Glucagon-like Peptide-1 Diabetes," US Endocrinology 7(2):104-109 (2011).
Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).
Roberts et al., "The Evolution of the Type I Interferons1," J. Interferon Cytokine Res. 18(10):805-816 (Oct. 1998).
Rohloff et al., "DUROS Technology Delivers Peptides and Proteins at Consistent Rate Continuously for 3 to 12 Months," J. Diabetes Sci. & Tech., 2(3):461-467 (May 1, 2008).
"Sequence Listings for International Patent Application Publication No. W02009109927, WIPO Patentscope", http://patentscope.wipo.int/search/docservicepdf_pct!id00000008776887, 1 page (last visited Nov. 14, 2012).
Shire et al., "Challenges in the Development of High Protein Concentration Formulations," J. Pharm. Sci. 93:1390-1402 (2004).
Smith, "Peripheral Neuro-hormones as a Strategy to Treat Obesity," oral presentation at the 2007 Cardiometabolic Health Congress in Boston, MA, pp. 1-35 (Sep. 26-29, 2007).
Written Opinion for International Patent Application No. PCT/US2009/005629 (corresponding to U.S. Appl. No. 12/587,946), 5 pages (Apr. 15, 2011).
Zhang et al., "Efficacy observations of different dosages of interferon to treat 150 Hepatitis B carriers," Current Physician 2(12):45-46 (1997).
"Abstracts 2007," Diabetologia Clinical & Experimental Diabetes & Metabolism, Springer, Berlin, Germany, vol. 50 S243 (Aug. 21, 2007) (paragraph [0586]) (XP002538652).
Jetschmann et al., "Open-label rising-dose study of omega interferon in IFN-naive patients with chronic hepatitis C," Gastroenterology 122:A278-A347 (Apr. 1, 2002) (Abstract M1454).
Bray, "Gut Signals and Energy Balance: Ghrelin, Peptide YY, Leptin, and Amylin," (Dec. 19, 2007) (slides and transcript for presentation at Medscape CME).
"Implantable infusion pumps: technology poised for takeoff," BBI Newsletter 17(12):209-211 (Dec. 1994).
Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).
Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).
Adolf et al., "Antigenic structure of human interferon ω1 (Interferon αII1): comparison with other human interferons," J. Gen. Virol. 68(6):1669-1676 (Jun. 1987).
Adolf et al., "Purification and characterization of natural human interferon ω1," J. Bio. Chem. 265(16):9290-9295 (Jun. 1990).

(56) References Cited

OTHER PUBLICATIONS

Adolf et al., "Human interferon ω1: isolation of the gene, expression in Chinese hamster ovary cells and characterization of the recombinant protein," Biochim. Biophys. Acta 108(9):167-174 (Jun. 1991).
ANDRX Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).
Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).
Aulitzky, "Successful Treatment of Metastatic Renal Cell Carcinoma With a Biologically Active Dose of Recombinant Interferon-Gama," Journal of Clinical Oncology 7(12):1875-1884 (1989).
Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan, D. et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," Journal of Pharmaceutical Science, 85(9):908-914 (1996).
Bakhtiar et al, "Taking Delivery," Soap Perfumery & Cosmetics 76(3):59-65 (2003) (liposomes in cosmetic delivery systems).
Balkwill, F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al, "Impact of moisture on thermally induced denaturation and decomposition of lyophilized bovine somatotropin," Drug Delivery Research & Dev. Biopolymers, (35):201-209 (1995).
Bell et al., "Hamster preproglucagon contains the sequence of glucagon and two related peptides," Nature 302:716-718 (1983).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).
Buckwold et al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).

Chang et al., "Biodegradeable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das, S. et al., "Reviewing Antisense Oligonucleotide Therapy: Part 2, Delivery Issues," BioPharm, 2(11):44-51 (1999).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-smotic acutation of implantable insulin micropumps," J. Biomed. Materials Res. 17:931-943 (1983).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel TiazofurinAnalogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(1-2):121-128 (2002).
Luft et al., "Electro-osmotic valve for the controlled administration of drugs," Med. & Biological Engineering & Computing 45-50 (Jan. 1978) (non-English with English abstract).

(56) References Cited

OTHER PUBLICATIONS

Gan To Kagaku Ryoho, "Phase II study of recombinant leukocyte A interferon (Ro22-8181) in malignant brain tumors," Cancer & Chemotherapy 12(4):913-920 (Apr. 1985) (non-English with English abtract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cystein for chronic hepatitis C: a placebo controlled double-blind multicentre study," J. Med. Virol. 61(4):439-442 (Aug. 2000).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima, N. et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
INTERMUNE® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).

Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon β-1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatits C: interferon alfa-2A trials," Hepatology 26: 89S-95S (Sep. 1997) (XP000981288).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).

(56) References Cited

OTHER PUBLICATIONS

Marincola et al., "Combination therapy with interferon alfa-2a and interleukin-2 for the treatment of metastatic cancer," J. Clinical Oncol. 13(5):1110-1122 (1995) (XP009078965).

Massey, "Interaction of vitamin E with saturated phospholipid bilayers," Biochem. & Biophys. Res. Comms. 106(3):842-847 (1982).

McHutchison et al., "Interferon α-2b alone or in combination with ribavirin as initial treatment for chronic hepatitis C," N. Engl. J. Med. 339(21):1485-1492 (Nov. 1998).

McHutchison, et al., "Open-label phase 1B study of hepatitis C viral dynamics with omega interferon treatment," Hepatology 34(4):A333 (Oct. 1, 2001) (XP004716177) (Abstract Only).

Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).

Milella et al., "Neutralizing antibodies to recombinant α-interferon and response to therapy in chronic hepatitis C infection," Liver 13(3):146-150 (Jun. 1993).

Mohler, "Primer on electrodeposited coatings," Materials Engineering 5:38-45 (1972).

Morgan, "Structure and Moisture Permeability of Film-Forming Poloyers," Ind. Eng. Chem. 45(10):2296-2306 (1953).

Motzer et al., "Phase I trial of 40-kd branched pegylated interferon alfa-2a for patients with advanced renal cell carcinoma," J. Clinical Oncol. 19(5):1312-1319 (2001).

Neumann et al., "Hepatitis C Viral Dynamics In Vivo and the Antiviral Efficacy of Interferon-alpha Therapy," Science 282:103-107 (Dec. 1998).

Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).

Norden et al., "Physicochemical characterization of a drug-containing phospholipid-stabilized o / w emulsion for intravenous administration," Eur. J. Pharm. Sci. 13(4):393-401 (2001).

Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).

Ortiz, A. et al., "A differential scanning calorimetry study of the interaction of α-tocopherol with mixtures of phospholipids," Biochim et Biophys Acta 898(2):214-222 (1987).

Panitch, "Interferons in multiple sclerosis," Drugs 44(6):946-962 (Dec. 1992).

Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).

Plauth et al, "Open-label phase II study of omega interferon in previously untreated HCV infected patients," Hepatology 34(4):A331 (Oct. 1, 2001) (XP004716169) (Abstract Only).

Plauth et al, "Open-label study of omega interferon in previously untreated HCV-infected patients," J. Hepatology 36(Supp. 1):125 (Apr. 2002) (XP002511882) (Abstract Only).

Poynard et al., "Is an 'a la carte' combined interferon α 2b plus ribavirin possible for the first line treatment in patients with chronic hepatitis C," Hepatology 31(1):211-218 (Jan. 2000).

Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).

Quesada et al., "Interferons in Hematological Malignancies", eds. Baron et al., U. Tex. 487-495 (1987).

Quintanar-Guerrero et al., "Applications of the ion-pair concept to hydrophilic substances with special emphasis on peptides," Pharm. Res. 14(2):119-127 (1997).

Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).

Roche Pharmaceuticals, Roferon®-A (Interferon alfa-2a, recombinant), 22 pages (2003).

Roff et al., "Handbook of Common Polymers", Cleveland Rubber Co. 72 pages (1971).

Rogers et al., "Permeability Valves," Ind. & Eng. Chem. 49(11):1933-1936 (Nov. 17, 1957).

Roman et al., "Cholestasis in the rat by means of intravenous administration of cyclosporine vehicle, Cremophor EL," Transplantation 48(4);554-558 (1989).

Roth et al., "High Dose Etretinate and Interferon-alpha—A Phase I Study in Squamous Cell Carcinomas and Transitional Cell Carcinomas," Acta Oncol. 38(5):613-617 (1999).

Roth et al., "Combination therapy with amylin and peptide YY[3-36] in obese rodents: anorexigenic synergy and weight loss additivity," Endocrinol. 148(12):6054-61 (Dec. 2007).

Schering Corp., Intron® A for Injection, 6 pages (2001).

Schering Corp., PEG-Intron™ (Peginterferon alfa-2b) Powder for Injection, 29 pages (2003).

Schmalfub, et al., "Modification of drug penetration into human skin using microemulsions," J. Controlled Release 46(3):279-285 (1997).

Sen et al., "The interferon system: a bird's eye view of its biochemistry," J. Biol. Chem. 267(8):5017-5020 (Mar. 1992).

Shiffman et al., "A decline in HCV-RNA level during interferon or ihterferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).

Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).

Shiratori et al., "Histologic improvement of fibrosis in patients with hepatitis C who have sustained response to interferon therapy," Ann. Int. Med. 132(7):517-524 (Apr. 2000).

Simon et al., "A longitudinal study of T1 hypointense lesions in relapsing MS: MSCRG trial of interferon β1a," Neurology 55(2):185-192 (Jul. 2000).

Sulkowskii et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).

Sulkowski, M., et al., "Peginterferon-α-2a (40kD) and ribavirin in patients with chronic hepatitis C: a phase II open label study," Biodrugs 16(2):105-109 (2002).

Talpaz et al., "Phase I study of polyethylene glycol formulation of interferon alpha-2B (Schering 54031) in Philadelphia chromosome-positive chronic myelogenous leukemia," Blood 98(6):1708-1713 (2001).

Talsania, T., et al., "Peripheral exendin-4 and peptide YY(3-36) synergistically reduce food intake through different mechanisms in mice," Endocrinology 146(9):3748-56 ( Sep. 2005).

Tanaka, H., et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).

Tong et al., "Prediction of response during interferon α 2b therapy in chronic hepatitis C patients using viral and biochemical characteristics: a comparison," Hepatology 26(6):1640-01645 (Dec. 1997).

Touza Rey et al., "The clinical response to interferon-γ in a patient with chronic granulomatous disease and brain abscesses due to Aspergillus fumigatus," Ann. Med. Int. 17(2):86-87 (Feb. 2000).

(56) References Cited

OTHER PUBLICATIONS

Trudeau et al., "A phase I study of recombinant human interferon alpha-2b combined with 5-fluorouracil and cisplatin in patients with advanced cancer," Cancer Chemother. Pharmacol. 35(6):496-500 (1995).

Tsung et al., "Preparation and Stabilization of Heparin/Gelatin Complex Coacervate Microcapsules," J. Pharm. Sci. 86(5):603-7 (May 1997).

Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).

Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).

Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).

Wang et al., "Ripple phases induced by α-tocopherol in saturated diacylphosphatidylcholines," Archives of Biochem. & Biophys. 377(2):304-314 (2000).

Wang et al., "The distribution of α-tocopherol in mixed aqueous dispersions of phosphatidylcholine and phosphatidylethanolamine," Biochimica et Biophysica Acta-Biomembranes 1509(1-2):361-372 (2000).

Wang et al, "Parenteral formulations of proteins and peptides: stability and stabilizers," J. Parenter. Sci. Technol. 42(2S):S4-S26 (1988).

Weinstock-Guttman et al., "What is new in the treatment of multiple sclerosis?" Drugs 59(3):401-410 (Mar. 2000).

Weissmann et al., "The interferon genes," Prog. Nucleic Acid Res. Mol. Biol. 33:251-300 (1986).

Wright et al., "Preliminary experience with α-2b-interferon therapy of viral hepatitis in liver allograft recipients," Transplantation 53(1):121-123 (Jan. 1992).

Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).

Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).

Yu et al., "Preparation, characterization, and in vivo evaluation of an oil suspension of a bovine growth hormone releasing factor analog," J. Pharm. Sci. 85(4):396-401 (1996).

Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).

Zein, "Interferons in the management of viral hepatitis," Cytokines Cell Mol. Ther. 4(4):229-241 (Dec. 1998).

Zeuzem et al., "Peginterferon Alfa-2a in Patients with Chronic Hepatitis C," New Engl. J. Med. 343(23):1666-1672 (2000).

Zeuzem et al., "Hepatitis C virus dynamics in vivo: effect of ribavirin and interferon α on viral turnover," Hepatology 28(1):245-252 (Jul. 1998).

Zhang et al., "Report on Large Dosage Interferon to Treat 30 Cases of Viral Encephalitis," J. Clinical Pediatrics 14(2):83-84 (1996).

Zhang et al, "A new strategy for enhancing the stability of lyophilized protein: the effect of the reconstitution medium on keratinocyte growth factor," Pharm. Res. 12(10):1447-1452 (1995).

Zheng et al. "Therapeutic Effect of Interferon Varied Dose in Treating Virus Encephalitis," Beijing Med. J. 13(2):80-81 (1998).

Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).

Office Action for U.S. Appl. No. 14/605,348, mailed Dec. 4, 2015, 14 pages.

Office Action for U.S. Appl. No. 14/632,700, mailed Dec. 18, 2015, 8 pages.

First Office Action for Chinese Patent Application No. 201410262400.X, mailed Dec. 14, 2015, 14 pages.

* cited by examiner

SOLVENT/POLYMER SOLUTIONS AS SUSPENSION VEHICLES

CROSS REFERENCE TO RELATED APPLICATION

The present application is a continuation of and claims priority to U.S. patent application Ser. No. 13/647,873, entitled "Solvent/Polymer Solutions as Suspension Vehicles," filed Oct. 9, 2012, which is a division of and claims priority to U.S. patent application Ser. No. 13/526,375, entitled "Solvent/Polymer Solutions as Suspension Vehicles," filed Jun. 18, 2012, now U.S. Pat. No. 8,440,226, issued May 14, 2013, which is a continuation of and claims priority to U.S. patent application Ser. No. 13/158,137, entitled "Solvent/Polymer Solutions as Suspension Vehicles," filed Jun. 10, 2011, now U.S. Pat. No. 8,206,745, issued Jun. 26, 2012, which is a continuation of and claims priority to U.S. patent application Ser. No. 11/347,562, entitled "Solvent/Polymer Solutions as Suspension Vehicles," filed Feb. 3, 2006, now U.S. Pat. No. 8,114,437, issued Feb. 14, 2012, which claims priority to and the benefit of U.S. Provisional Patent Application Ser. No. 60/650,225, filed Feb. 3, 2005. The contents of each of the above-identified applications are incorporated herein by reference in their entirety.

FIELD OF THE INVENTION

The present invention relates to a suspension vehicle capable of uniformly dispersing an active agent and delivering the active agent at a low flow rate. More specifically, the present invention relates to a suspension vehicle that includes a solvent and a polymer and is formulated to exhibit phase separation upon contact with an aqueous environment.

BACKGROUND OF THE INVENTION

There is considerable interest in delivering small molecules or biomolecular substances, such as peptides, polypeptides, proteins, lipoproteins, nucleic acid, hormones, viruses, or antibodies, using implantable drug delivery devices, such as osmotic, mechanical, or electromechanical devices. Implantable drug delivery devices provide improved patient compliance because the devices are not easily tampered with by a patient and are designed to provide therapeutic doses of the biomolecular substance over extended periods of time, such as weeks, months, or even years. Use of the implantable drag delivery device also provides reduced irritation at the site of the implantation compared to daily or multiple injections, fewer occupational hazards for the patients and practitioners, and reduced waste disposal hazards. Implantable drug delivery devices that are capable of delivering a desired dose of a beneficial agent over extended periods of time are known in the art.

However, delivering the biomolecular substance with the implantable drug delivery device is problematic. While the biomolecular substance is active in an aqueous environment, it is only marginally stable in en aqueous environment under ambient conditions. Therefore, a formulation of the biomolecular substance typically requires refrigeration, otherwise it begins to degrade. The biomolecular substance degrades by one or more mechanisms including deamidation, oxidation, hydrolysis, disulfide, interchange, or racemization. Significantly, water is a reactant in many of the degradation pathways. In addition, water acts as a plasticizer and facilitates the unfolding and irreversible aggregation of the biomolecular substance. To overcome the stability problems with aqueous formulations of the biomolecular substance, dry powder formulations of the biomolecular substance have been created using known particle formation processes, such as lyophilization, spray-drying, freeze-drying, or desiccation of the biomolecular substance. While dry formulations of the biomolecular substances are stable, many delivery methods require flowable forms of the biomolecular substance. For instance, flowable forms are needed for parenteral injections and implantable drug delivery devices.

To form a flowable formulation, a dry, powdered biomolecular substance is typically suspended in a nonaqueous, viscous vehicle. The biomolecular substance must be contained within a formulation that maintains the stability of the biomolecular substance at an elevated temperature (i.e., 37° C. and above) over the operational life of the implantable drug delivery device. The biomolecular substance must also be formulated to allow delivery of the biomolecular substance into a desired environment of operation over an extended period of time. The biomolecular substance must also be formulated to allow delivery at a low flow rate (i.e., less than or equal to approximately 100 µl/day).

U.S. Pat. No. 6,468,961 to Brodbeck, et al, and United States Patent Application Nos. 2001/0024069 and 2004/0151753, to both Chen, et al., disclose a depot composition that includes a viscous gel formed from a polymer and a solvent. The polymer is a polylactide, polyglycolide, caprolactone-based polymer, polycaprolactone, polyanhydride, polyamine, polyurethane, polyesteramide, polyorthoester, polydioxanone, polyacetal, polyketal, polycarbonate, polyorthocarbonate, polyphosphazene, succinate, poly(malic acid), poly(amino acid), polyvinylpyrrolidone (PVP), polyethylene glycol, polyhydroxycellulose, hydroxymethylcellulose, polyphosphoester, polyester, polyoxaester, polybutylene terephthalate, polysaccharide, chitin, chitosan, hyaluronic acid, or copolymer, terpolymer, or mixtures thereof. The solvent includes aromatic alcohols, esters of aromatic acids, such as lower alkyl or aralkyl esters of aryl acids; aromatic ketones, such as aryl, aralkyl, or lower alkyl ketones; and mixtures thereof.

United States Patent Application No. 2003/0108609 to Berry, et al., discloses a stable, nonaqueous single-phase viscous vehicle that includes at least two of a polymer, a solvent, and a surfactant. The vehicle suspends a beneficial agent, which is deliverable at a low flow rate and at body temperature form an implantable drug delivery device. The solvent includes carboxylic acid esters, polyhydric alcohols, polymers of polyhydric alcohols, fatty acids, oils, lauryl alcohol, or esters of polyhydric alcohols. The polymer includes polyesters, pyrrolidones, esters or ethers of unsaturated alcohols, or polyoxyethylenepolyoxpropylene block copolymers. The vehicle is well suited to preparing suspensions that include biomolecular beneficial agents and are stable over extended periods of time, even at elevated temperatures. However, under certain circumstances, a formulation of the vehicle and the beneficial agent may have the potential to inhibit delivery of the beneficial agent into the desired environment of operation. In particular, when the formulation is exposed to an aqueous liquid, such as a physiological fluid, within a delivery conduit of a device used to deliver the formulation, the polymer partitions into the aqueous liquid, the concentration of the polymer within the aqueous liquid may increase to such an extent that a highly viscous polymer gel is formed within the delivery conduit, which results in a partial or complete occlusion of the delivery conduit and interferes with the desired operation of the delivery device. The potential for such occlusions increases where the geometry of the delivery conduit is such that aqueous liquid interfaces with the drug formulation in a confined area over a relatively long period of time (e.g., hours or days).

It would be an improvement in the art to provide a vehicle that facilitates delivery of a formulation of a small molecule or biomolecular substance from a depot composition or an implanted drug delivery device. Ideally, the vehicle is formulated to deliver the therapeutic agent at a controlled rate without blocking or occluding the drug delivery device and/or to maintain the stability of the biomolecular substance over an extended period of time.

BRIEF SUMMARY OF THE INVENTION

The present invention relates to a nonaqueous, single-phase vehicle that is capable of suspending an active agent. The nonaqueous, single-phase vehicle includes at least one solvent and at least one polymer, and is formulated to exhibit phase separation upon contact with an aqueous environment. The at least one solvent may be immiscible with water and the at least one polymer may be soluble in the at least one solvent. The at least one solvent may be selected from the group consisting of benzyl benzoate, decanol, ethyl hexyl lactate, and mixtures thereof. The at least one polymer may be selected from the group consisting of a polyester, pyrrolidone, ester of an unsaturated alcohol, ether of an unsaturated alcohol, polyoxyethylenepolyoxypropylene block copolymer, and mixtures thereof. In one embodiment, the at least one solvent is benzyl benzoate and the at least one polymer is polyvinylpyrrolidone (PVP).

The present invention also relates to a stable, nonaqueous suspension formulation that includes an active agent and a nonaqueous, single-phase vehicle. The nonaqueous, single-phase vehicle includes at least one solvent and at least one polymer and is formulated to exhibit phase separation upon contact with an aqueous environment. The at least one solvent and the at least one polymer may be one of the materials described above. The active agent may be selected from the group consisting of baclofen, glial-cell line-derived neurotrophic factor, a neurotrophic factor, conatonkin G, Ziconotide, clonidine, axokine, an antisense oligonucleotide, adrenocorticotropic hormone, angiotensin I, angiotensin II, atrial natriuretic peptide, B-natriuretic peptide, bombesin, bradykinin, calcitonin, cerebellin, dynorphin N, alpha endorphin, beta endorphin, endothelin, enkephalin, epidermal growth factor, fertirelin, follicular gonadotropin releasing peptide, galanin, glucagon, glucagon-like peptide-1, gonadorelin, gonadotropin, goserelin, growth hormone releasing peptide, histrelin, human growth hormone, insulin, an alpha-, beta-, or omega-interferon, Nesiritide, leuprolide, luteinizing hormone-releasing hormone, motilin, nafarerlin, neurotension, oxylocin, relaxin, soniatostatin, substance P, tumor necrosis factor, triptorelin, vasopressin, growth hormone, nerve growth factor, a blood clotting factor, and a ribozyme. In one embodiment, the at least one solvent is benzyl benzoate, the at least one polymer is polyvinylpyrrolidone, and the active agent is omega interferon (omega-IFN). The active agent may also be selected from small molecules such as, for example, ocaperidone, risperidone, and paliperidone.

The present invention also relates to a method of preparing a stable, nonaqueous suspension formulation. The method includes providing a nonaqueous, single-phase vehicle that includes at least one polymer and at least one solvent. The nonaqueous, single-phase vehicle exhibits phase separation upon contact with an aqueous environment. An active agent is provided, wherein the active agent is substantially insoluble in the nonaqueous, single-phase vehicle. The active agent and the nonaqueous, single-phase vehicle are mixed to form a stable nonaqueous suspension formulation. The at least one solvent, the at least one polymer, and the active agent may be one of the materials described above.

BRIEF DESCRIPTION OF THE SEVERAL VIEW OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
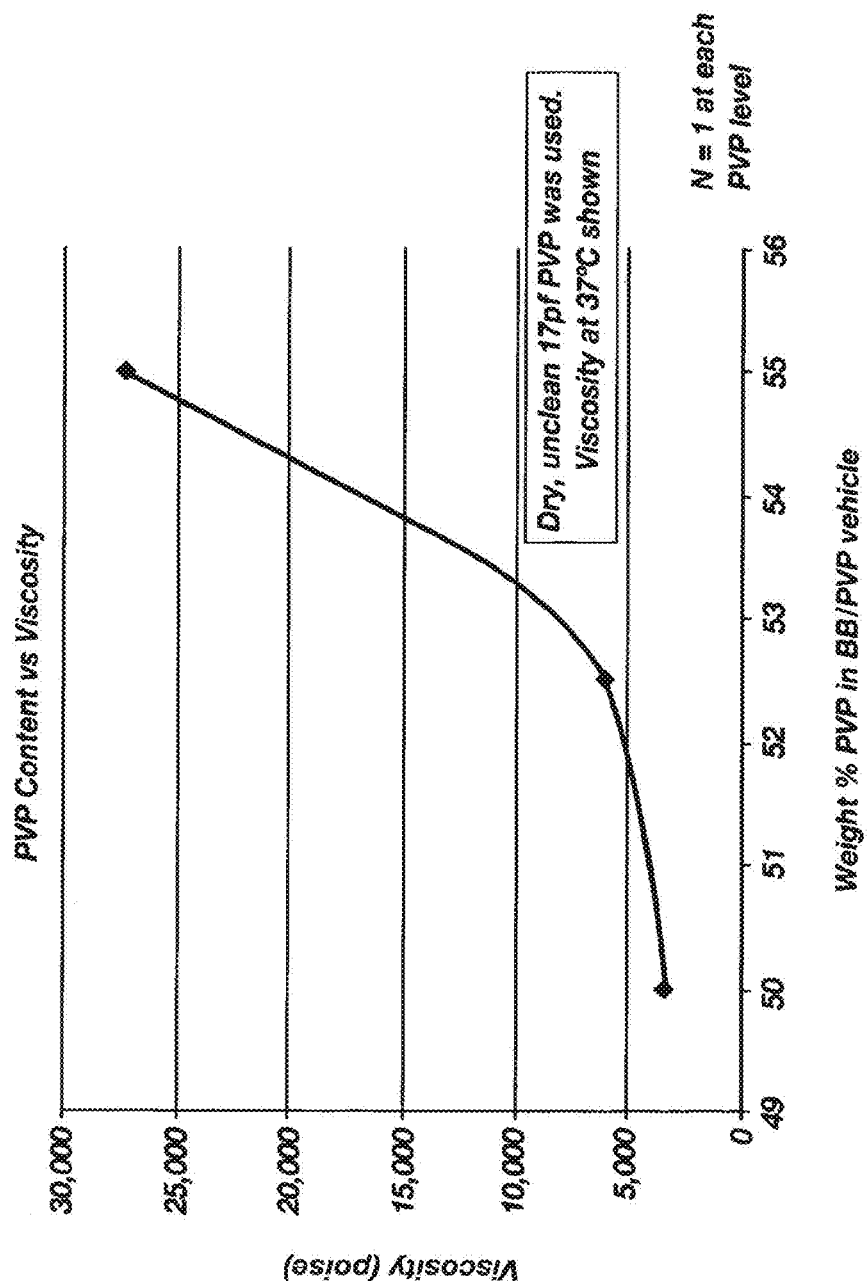
FIG. 1 is a graph illustrating the viscosity of a suspension vehicle that includes benzyl benzoate and PVP as a function of the weight percentage of PVP.

A suspension formulation having a suspension vehicle and an active agent is disclosed. The suspension vehicle is formulated to exhibit phase separation upon contact with an aqueous environment. As used herein, the phrase "phase separation" refers to the formation of multiple phases (e.g., liquid or gel phase) in the suspension vehicle, such as when the suspension vehicle contacts the aqueous environment. In specific embodiments of the invention, the suspension vehicle is formulated to exhibit phase separation upon contact with an aqueous environment having less than approximately 10% water. The suspension vehicle is a single-phase vehicle in which the active agent is dispersed. As used herein, the phrase "single-phase" refers to a solid, semisolid, or liquid homogeneous system that is physically and chemically uniform throughout, as determined by differential scanning calorimetry (DSC). As used herein, the term "dispersed" refers to dissolving, dispersing, suspending, or otherwise distributing the active agent in the suspension vehicle. The suspension vehicle is formulated to provide sustained delivery of the active agent to a patent by delivering the active agent at a low flow rate over an extended period of time. As used herein, the term "patient" refers to a human or another mammal to which the suspension formulation is administered.

The suspension vehicle provides a stable environment in which the active agent is dispersed. The suspension vehicle includes at least one polymer and at least one solvent, forming a solution of sufficient viscosity to uniformly suspend particles of the active agent. The viscosity of the suspension vehicle may prevent the active agent from settling during storage and use of the suspension formulation in, for example, an implantable, drug delivery device. The suspension vehicle is biodegradable in that the suspension vehicle disintegrates or breaks down over a period of tone in response to a biological environment. The disintegration of the suspension vehicle may occur by one or more physical or chemical degradative processes, such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the patient.

The solvent in which the polymer is dissolved may affect characteristics of the suspension formulation, such as the behavior of the active agent during storage and, where applicable, use of the implantable, drug delivery device. The solvent may be selected in combination with the polymer so that the resulting suspension vehicle exhibits phase separation upon contact with the aqueous environment. Optionally, the solvent may be selected in combination with the polymer so that the resulting suspension vehicle exhibits phase separation upon contact with the aqueous environment having less than approximately 10% water. The solvent may be a pharmaceutically acceptable solvent that is not miscible with water. The solvent may also be selected so that she polymer is soluble in the solvent at high concentrations, such as at a polymer concentration of greater than approximately 30%. However, the active agent may be substantially insoluble in the solvent. The solvent may include, but is not limited to, lauryl alcohol, benzyl benzoate, benzyl alcohol, lauryl lactate, CERAPHYL® 31, decanol (also called decyl alcohol), ethyl hexyl lactate, and long chain (C8 to C24) aliphatic alcohols, esters, or mixtures thereof. The solvent used in the suspension vehicle may be "dry," in that it has a low moisture content. In one embodiment, the solvent is benzyl benzoate, which has a solubility in water of less than approximately 0.01%. Using benzyl benzoate as the solvent can be advantageous because benzyl benzoate is used as an excipient in injectable products such as DELESTROGEN® and FASLODEX®. As such, the risk of the patient suffering adverse reactions to benzyl benzoate is reduced and the cost to demonstrate safety of the benzyl benzoate is decreased.

The polymer may include, but is not limited to, a polyester, pyrrolidone, ester or ether of an unsaturated alcohol, polyoxyethylenepolyoxypropylene block copolymer, or mixtures thereof. The polyester may be polylactic acid or polylacticpolyglycolic acid. The pyrrolidone may be PVP having a molecular weight ranging from approximately 2,000 to approximately 1,000,000. The ester or ether of the unsaturated alcohol may be vinyl acetate. In one embodiment, the polymer is PVP. The polymer used in the suspension vehicle may include one or more different polymers or may include different grades of a single polymer. The polymer used in the suspension vehicle may also be dry or have a low moisture content.

The polymer and the solvent may each be present in the suspension vehicle in an amount sufficient to provide the desired performance of the suspension vehicle. The polymer may be present in the suspension vehicle from approximately 10% to approximately 90% and the solvent may be present from approximately 10% to approximately 90%. The percentages of the polymer and the solvent are provided herein in terms of wt/wt ratios. For instance, the suspension vehicle may include from approximately 25% to approximately 75% of the polymer and from approximately 25% to approximately 75% of the solvent. In one embodiment, the suspension vehicle includes from approximately 40% to approximately 60% of the polymer and from approximately 40% to approximately 60% of the solvent.

The suspension vehicle may exhibit Newtonian behavior. The suspension vehicle is formulated to provide a viscosity that maintains the uniform dispersion of the active agent for a predetermined period of time, which facilitates creation of a suspension formulation that is tailored to provide controlled delivery of the active agent at a desired rate. The viscosity of the suspension vehicle may vary depending on the desired application, the size and type of the active agent, and the loading of the active agent in the suspension vehicle. The viscosity of the suspension vehicle may be varied by altering the type or relative amount of the solvent or polymer used. The suspension vehicle may have a viscosity ranging from approximately 100 poise to approximately 1,000,000 pose, such as from approximately 1,000 poise to approximately 100,000 poise. The viscosity is measured at 37° C., at a shear rate of $10^{-4}$/sec, using a parallel plate rheometer. In one embodiment, the viscosity of the suspension vehicle ranges from approximately 5,000 poise to approximately 50,000 poise. While the suspension vehicle exhibits phase separation when contacted with the aqueous environment, the suspension vehicle may exhibit substantially no phase separation as a function of temperature. For instance, at a temperature ranging from approximately 0° C. to approximately 70° C. and upon temperature cycling, such as cycling from 4° C. to 37° C. to 4° C., the suspension vehicle may exhibit no phase separation. In particular embodiments of the invention, the suspension vehicle exhibits phase separation when contacted with the aqueous environment having less than approximately 10% water.

The suspension vehicle may be prepared by combining the polymer and the solvent under dry conditions, such as in a drybox. The polymer and solvent may be combined at an elevated temperature, such as front approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. DSC may be used to verify that the suspension vehicle is a single phase.

The active agent may be added to the suspension vehicle to form the suspension formulation. The active agent may be a biomolecular substance that has biological activity or is capable of being used to treat a disease or other pathological condition. The active agent may include, but is not limited to, a peptide, polypeptide, protein, amino acids, nucleotides, a polymer of an amino acid residue(s) or a nucleotide residue(s), hormone, virus, antibody, or mixtures thereof. The biomolecular substance may also be a conjugated protein, such as a lipoprotein or post translationally modified form thereof, such as a glycosylated protein or a protein substance having D-amino acids, modified, derivatized, or non-naturally occurring amino acids in the D- or L-configuration and/or peptomimetic units. The biomolecular substance may be naturally derived, synthetically produced, or recombinantly produced. The active agent may also be an organic compound, such as a drug, medicine, vitamin, nutrient, or food supplement. The active agent may be used in a solid state, such as a powder, crystalline, or amorphous state. As such, the active agent may be dry or may have a low moisture content. The active agent may be stable at ambient and physiological temperatures in the solid state. The active agent may also be used in the form of a pharmaceutically acceptable salt, such as a salt of an inorganic acid, an organic acid, an inorganic base, or an organic base. As previously mentioned, the active agent may have little or no solubility in the suspension vehicle. The active agent can be selected to provide a therapeutic or beneficial effect when administered to the patient. For the sake of example only, the active agent may be used as a treatment for Hepatitis C, heart disease, diabetes, cancer, bone disease, autoimmune disease, gastrointestinal diseases, respiratory disease, kidney disease, liver disease, circulatory diseases, blood disorders, hormonal disorders, genetic disorders, metabolic disorders, thyroid disease, or central nervous system disorders.

Examples of active agents that may be utilized in the suspension formulation include, but are not limited to, baclofen, glial-cell line-derived neurotrophic factor (GDNF), neurotrophic factors, conatonkin G, Ziconotide, clonidine, axokine, antisense oligonucleotides, adrenocorticotropic hormone, angiotensin I and II, atrial natriuretic peptide, B-natriuretic peptide (BNP), bombesin, bradykinin, calcitonin, cerebellin, dynorphin N, alpha and beta endorphin, endothelin, enkephalin, epidermal growth factor, fertirclin, follicular gonadotropin releasing peptide, galanin, glucagon, glucagon-like peptide (GLP)-1, gonadorelin, gonadotropin, goserelin, growth hormone releasing peptide, histrelin, human growth hormone, insulin, interferons (IFN), such as omega-IFN, leuprolide, Nesiritide, luteinizing hormone-releasing hormone (LHRH), motilin, natarerlin, neurotensin, oxytocin, relaxin, somatostatin, substance P, tumor necrosis factor, triptorelin, vasopressin, growth hormone, nerve growth factor, blood clotting factors, and ribozymes. The active agent may also be selected from small molecules such as, for example, ocaperidone, risperidone, and paliperidone. Analogs, derivatives, antagonists, agonists, and pharmaceutically acceptable salts of the active agents mentioned above may also be used. In one embodiment the active agent is omega-IFN.

The amount of the active agent present in the suspension formulation may vary depending on the potency of the active agent, the disease or condition to be treated, the solubility of the active agent, the dose to be administered, the duration of administration, and the desired release rate. The active agent may be present in the suspension formulation in an amount that ranges from approximately 0.1% (w/w) so approximately 50% (w/w). The suspension formulation may include from approximately 50% (w/w) to 99.9% (w/w) of the suspension vehicle. In one embodiment, the particle containing the active agent is present in the suspension formulation at approximately 3-12% 10% (w/w).

The active agent used in the suspension formulation may be provided as a stabilized, dry powder that is produced by spray-drying, freeze-drying, a supercritical fluid process, desiccation, granulation, grinding, adding, precipitation, homogenization, or a coating process, as known, in the art. To provide the active agent as the dry powder, the active agent may be formulated with one or more adjuvants, excipients, stabilizers, bulking agents, preservatives, or coating agents, as known in the art. For instance, the active agent may be formulated with at least one of citrate, histidine, succinate methionine, sucrose, and dextran. In one embodiment, the suspension formulation includes omega-IFN:sucrose:methionine:citrate at a ratio of 1:2:1:2.15.

The suspension formulation may be used in the implantable, drug delivery device to provide sustained delivery of the active agent over an extended period of time, such as over weeks, months, or up to approximately one year. The suspension formulation may be prepared by dispersing the active agent in the suspension vehicle. The suspension vehicle may be heated and the active agent added to the suspension vehicle under dry conditions. The ingredients may be mixed under vacuum at an elevated temperature, such as from approximately 40° C. to approximately 70° C. The ingredients may be mixed at a sufficient speed, such as from approximately 40 rpm to approximately 120 rpm, and for a sufficient amount of time, such as approximately 15 minutes, to achieve a uniform dispersion of the active agent in the suspension vehicle. The mixer may be a dual helix blade or other suitable mixer. The reaching mixture may be removed from the mixer, sealed in a dry container to prevent water from contaminating the suspension formulation, and allowed to cool to room temperature before loading into the implantable, drug delivery device. The suspension formulation may be loaded into the implantable, drug delivery device by conventional techniques. The resulting suspension formulation may be stable when stored at elevated temperatures or for an extended period of time.

The suspension formulation may also be used in the form of depot injections to provide sustained delivery of biologically active macromolecules and small molecule compounds. The suspension formulation may be designed to deliver agents for periods of days to months. Alternatively, the suspension formulation may be loaded into an implantable, drug delivery device, which may be capable of delivering the active agent at a desired flow rate over a desired period of time. For example, the suspension formulation may be delivered by an osmotically, mechanically, electromechanically, or chemically driven drug delivery devices. The flow rate at which the active agent is delivered may be less than approximately 100 µl/day, such as from approximately 0.5 µl/day to approximately 5 µl/day. The active agent may be delivered over a period ranging from more than approximately one week to approximately one year or more. The implantable, drug delivery device may include a reservoir having at least one orifice through which to active agent is delivered. The suspension formulation may be stored within the reservoir. The suspension formulation may also be delivered born a drug delivery device that is not implantable or implanted. In one embodiment, the implantable, drug delivery device is osmotically driven, such as a DUROS® implant, which is available from ALZA Corp. (Mountain View, Calif.). The DUROS® implant may enable continuous delivery of the active agent for an extended duration, such as for up to approximately one year.

Other exemplary implantable, drug delivery devices may include regulator-type implantable pumps that provide constant flow, adjustable flow, or programmable flow of the active agent, such as those available from Codman & Shurtleff, Inc. (Raynham, Mass.), Medtronic, Inc. (Minneapolis, Minn.), and Tricumed Medinzintechnik GmbH (Germany).

Phase separation of the suspension vehicle may occur when the suspension vehicle contacts the aqueous environment, forming a second phase that is rich in water and the polymer. The second phase includes substantially no solvent. Since the active agent is stable in nonaqueous and dilute aqueous environments, the active agent may remain stably dispersed after the phase separation occurs. In contrast, the active agent is not stable in environments that include moderate quantities of water, such as from approximately 10% to 25% water.

In a particular embodiment where a drug delivery device is implanted in the patient, water from surrounding tissues may enter one end of the implantable, drug delivery device through a semipermeable membrane. The water may also cause an osmotic engine in the implantable, drug delivery device to swell, displacing a piston and releasing the suspension formulation from a second end of the implantable, drug delivery device and into the patient's body.

Without being bound to any theory, it is believed that the suspension vehicle is capable of effectively delivering the active agent to the patient due to the environment that the active agent encounters as the active agent transitions from the dry suspension formulation to the dilute aqueous environment. If the suspension vehicle is incorporated into an implantable, drug delivery device, the suspension vehicle is capable of effectively delivering the active agent to the patient due to the environment that the active agent encounters as the active agent traditions from the dry suspension formulation within the implantable, drug delivery device to the dilute aqueous environment outside of the implantable drug delivery device.

The following examples serve to explain embodiments of the present invention in more detail. These examples are not to be construed as being exhaustive or exclusive as to the scope of this invention.

EXAMPLES

Example 1

Stability and In Vitro Release of Omega-IFN in a Benzyl Benzoate and a Benzyl Benzoate/Benzyl Alcohol Suspension Vehicle The stability of omega-IFN for three months at 40° C. in two suspension vehicles was determined. One of the suspension vehicles included PVP dissolved in benzyl benzoate. The second suspension vehicle included PVP dissolved in a 90/10 benzyl benzoate/benzyl alcohol mixture. A release race study at 37° C. was also performed. The materials used in the stability and release rate studies are shown in Table 1.

TABLE 1

Materials To Be Used in the Stability and Release Rate Studies

Spray-dried omega-IFN: sucrose:methionine:citrate (1:2:1) in 25 mM citrate buffer
Benzyl benzoate (BB)
Benzyl alcohol (BA)
Polyvinylpyrrolidone (PVP)
Citrate Buffer
Phosphate Buffered Saline (PBS)
Piston, fluoroelastomer TABLE 1-continued Materials To Be Used in the Stability and Release Rate Studies DUROS ® Osmotic Tablet
Tecophilic HP-60D-33 Membrane (g2) Blue NB 7443:155
Titanium Reservoir (g2)
Polyethylene Glycol 400
Silicone Fluid, MDM 350
Spiral Diffusion Moderator (DM), high density polyethylene (HDPE), 10 mil, 0.43 mm
10 cc OSGE Glass Syringes To produce the spray-dried omega-IFN, omega-IFN was combined with sucrose and methionine dissolved in a 25 mM pH 6.0 citrate buffer and then spray-dried. Spray-drying was conducted and particles collected in a clean, dry air isolator. Particles were tested for purity, protein content, moisture content, oxidation, deamidation, degradation, aggregation, and particle size distribution, as known in the art.

Since in the solvents are likely to contain peroxide residues, the peroxides were removed from the benzyl benzoate and benzyl alcohol before preparing the suspension vehicle. To remove the peroxides, alumina was mixed with each of the benzyl benzoate and benzyl alcohol for 30 minutes. The solvents were then filtered through a 0.2 µm filter and stored in a sealed vial under nitrogen. The peroxide levels were measured for each of the benzyl benzoate and benzyl alcohol, as known in the art, before using the solvents in the suspension vehicle. Before use, the PVP was treated with a solution of methionine to reduce the peroxide content. The solution was then diafiltered to remove the methionine, and lyophilized to remove water, leaving a cake of the PVP Peroxide levels in the PVP were measured as known in the art.

The suspension vehicle was prepared in a DIT mixer at 65° C. The water bath temperature was set to approximately 65° C. and the mixer was preheated. Appropriate amounts of the benzyl benzoate and/or benzyl alcohol were weighed into the mixing bowl. An appropriate amount of the PVP was weighed and transferred into the mixing bowl. The mixing bowl was mounted and the ingredients stirred to incorporate the PVP into the solvent. A vacuum (−5 to −10 in Hg) was applied during the mixing. Alter the PVP was visually incorporated into the solvent, the vacuum was increased to −30 in Hg, the bowl temperature adjusted to 60° C., and the ingredients were mixed for two hours. The suspension vehicle was discharged into a glass jar and degassed in a vacuum oven set at 60° C. and −30 in Hg for approximately 4-6 hours. The solvent PVP ratio was selected so that the suspension vehicle had a viscosity of between 10,000 poise and 20,000 poise. As shown in FIG. 1, the viscosity of the BB/PVP suspension vehicle is within the desired range.

The suspension formulation including the suspension vehicle and the omega-IFN particles was prepared in a drybox under nitrogen. A hot plate was moved into the drybox and preheated to 60° C. Appropriate amounts of the omega-IFN and the suspension vehicle were weighed into a glass beaker. Using a stainless steel spatula, the omega-IFN particles were manually incorporated into the suspension vehicle while warming the suspension vehicle with the hotplate. The suspension formulation was mixed by hand for 15 minutes. The suspension formulation included 1:2:1 omega-IFN:sucrose:methionine by weight with 25 mM citrate buffer. The particle loading of omega-IFN in the suspension was approximately 10%, which is equivalent to a drug loading of approximately 1.7%. This is consistent with a unit dose of 25 μg/day of the omega IFN.

Using a spatula, the suspension formulation was filled into a 10 mL OSGE syringe and the syringe plunger inserted to seal the syringe. An oven was preheated to 60° C. and the filled syringe was transferred to the vacuum oven while a nitrogen flow was on to purge the vacuum oven of oxygen. The plunger was removed and a deaeration spring inserted into the syringe. The formulation was allowed to equilibrate to oven temperature. The spring was rotated at a target of 100 rpm and a vacuum slowly applied until approximately −30 in Hg was attained. The spring was used to mix the suspension formulation for 30 minutes under vacuum. After deaeration, the plunger was inserted into the syringe and excess air was removed. The syringe was sealed in polyfoil and stored refrigerated (at 2° C.-8° C.).

System samples for the release rate and stability studies were filled on the benchtop under ambient conditions. To form the systems, subassemblies were produced by lubricating the reservoirs and pistons with SMF 350. The piston was inserted into the reservoir and ~20 μL of PEG400 was dispensed on the piston. Two osmotic tables were inserted into the subassembly and an annealed and dried membrane was inserted into the reservoir. The subassemblies were annealed for 30 minutes at 65° C. A filling needle was attached to the syringe containing the suspension formulation. The glass syringe was loaded into a Harvard syringe pump with a heating block surrounding the barrel of the syringe and heated to 65° C. The subassembly was placed on the needle and the implant reservoir filled to within approximately ¼" of the end. Aliquots of the suspension formulation for stability testing were dispensed into glass vials. The vials were flushed with nitrogen, capped, sealed, and stored at 40° C.

To test the systems, the membrane end was placed into a stoppered VACUTAINER® with 3 mL of PBS (phosphate buffer) and the capillary or diffusion moderator end of the assembly was placed into a dry vial (primed) or a vial filled with 3 mL of citrate buffer (unprinted). The system was placed into a 37° C. oven or water bath. For primed systems, the diffusion moderator side vial was filled with citrate buffer after the suspension formulation was observed to exit from the implants (several days to 1 week). For primed systems, the buffer vial was replaced with a new vial containing fresh buffer one day after filling the diffusion moderator side vial. The old vial was submitted for protein assay. Once per week, the vial was removed from the diffusion moderator of the system for protein assay determination. A new vial with buffer was placed onto the system and the implant returned to 37° C. The samples for protein assay were stored in a refrigerator at 4° C.

Figure 2:
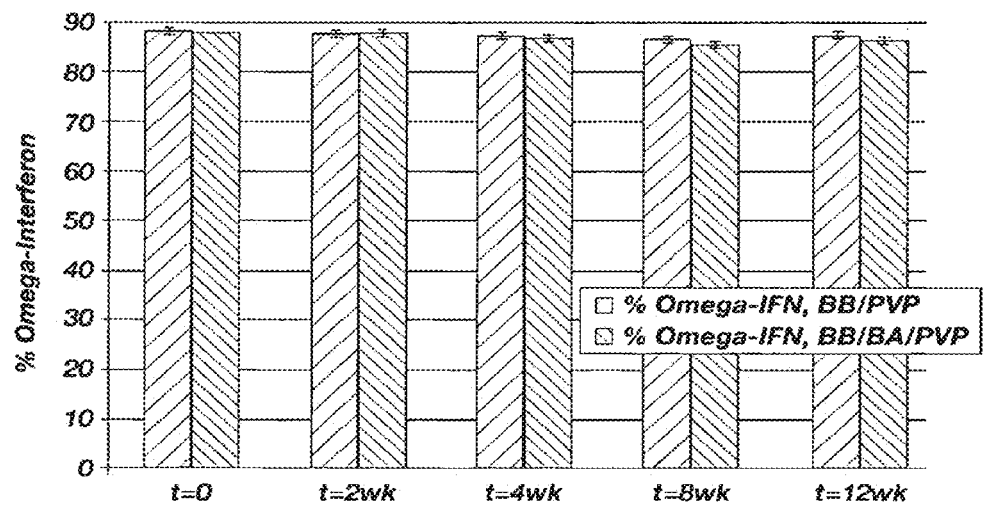
FIG. 2 illustrates the percentage of total omega-IFN that appears as the unaltered omega-IFN main peak in suspension vehicles that include (i) benzyl benzoate and PVP and (ii) benzyl benzoate, benzyl alcohol, and PVP at 40° C. as a function of time.
Figure 3:
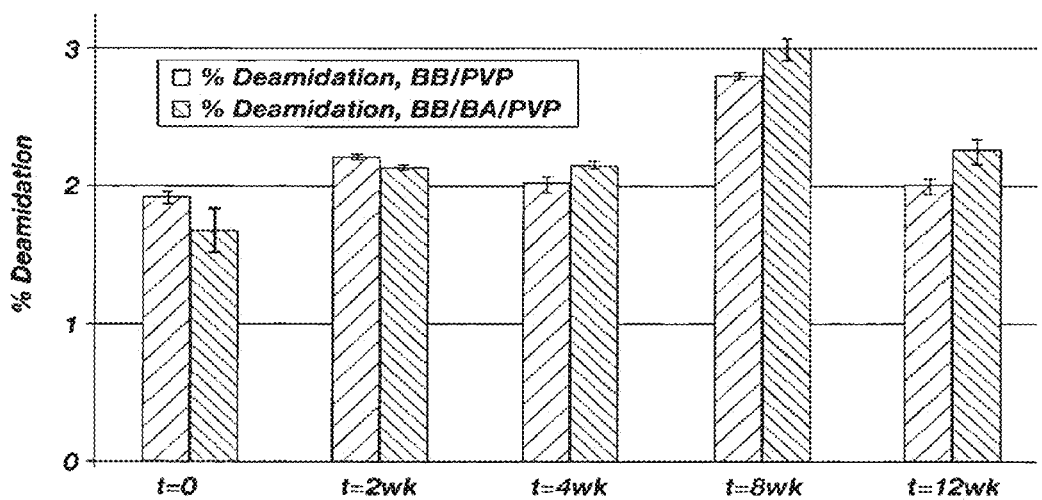
FIG. 3 illustrates the percentage of the total omega-IFN present in the suspension vehicle that is in the deamidated state in suspension vehicles that include (i) benzyl benzoate and PVP and (ii) benzyl benzoate, benzyl alcohol, and PVP at 40° C. as a function of time.
Figure 4:
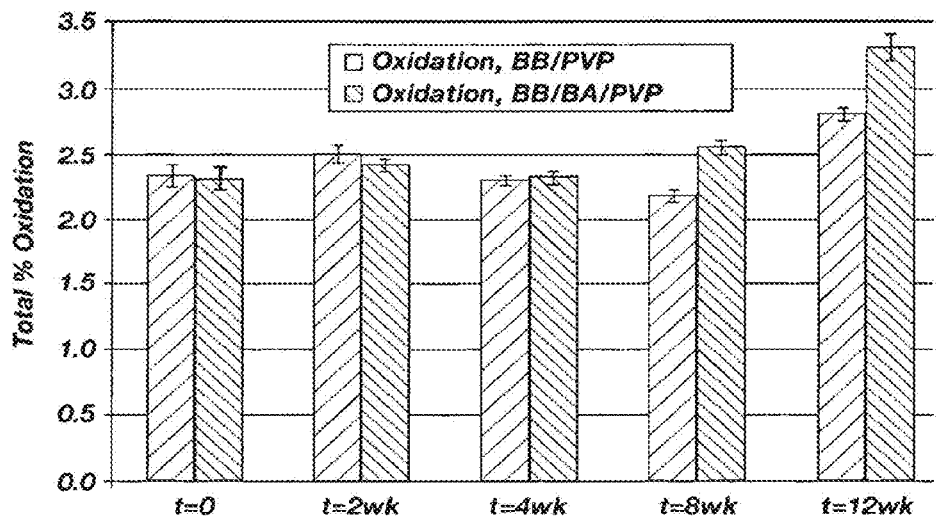
FIG. 4 illustrates the total percentage of the total omega-IFN present in the suspension vehicle that is in the oxidated state in suspension vehicles that include (i) benzyl-time.
Figure 5:
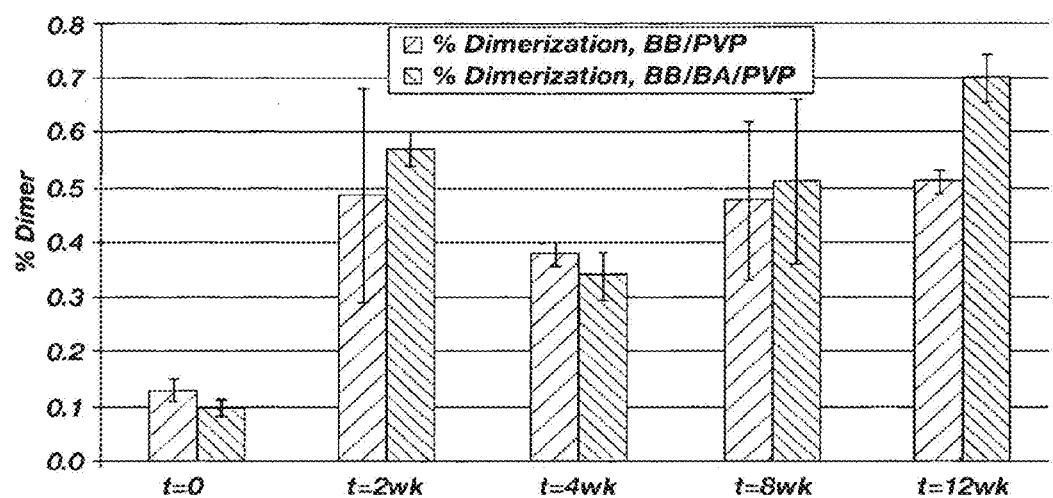
FIG. 5 illustrates the percentage of dimerization of omega-IFN in suspension vehicles that include (i) benzyl benzoate and PVP and (ii) benzyl benzoate, benzyl alcohol, and PVP at 40° C. as a function of time.

The stability of the omega-IFN in the suspension formulation was measured after storage at 40° C. in glass vials flushed with nitrogen. The stability samples were tested in triplicate at t−0, 2, 4, 8, and 12 weeks. The samples were analyzed using reversed-phase high pressure liquid chromatography (RP-HPLC) to determine purity with respect to oxidation and deamidation and using size exclusion chromatography (SEC) to determine purity with respect to aggregation and precipitation. As shown in FIG. 2, the measured levels of omega-IFN did not change over time in the benzyl benzoate/PVP suspension vehicle. In addition, as shown in FIG. 3, deamidation of the omega-IFN was unchanged between 0 and 12 weeks. Oxidation of the omega-IFN was also unchanged between 0 and 8 weeks but increased slightly after 12 weeks, as shown in FIG. 4. Dimerization levels of the omega-IFN increased from 0 to 2 weeks but did not increase from 2 to 12 weeks, as shown in FIG. 5.

A rate at which the suspension vehicles released the omega-IFN into an aqueous medium at 37° C. was determined. The release tare study was performed using the systems described above. The spiral diffusion moderator was formed from HDPE having an internal diameter of 0.43 mm and a path length of 5 cm. The groups and group size in the release rate study are shown in Table 2.

TABLE 2

Release Rate Experimental Plan

| Start-up Conditions | Suspension 191-1 BB/PVP |
|---|---|
| Dry start, spiral DM | 12 |
| Wet start, spiral DM | 12 |

The citrate buffer included 50 mM citric acid at pH 2 with 0.2% sodium azide added as an antibacterial agent. In all systems, the membrane side of the system is exposed to PBS.

Figure 6:
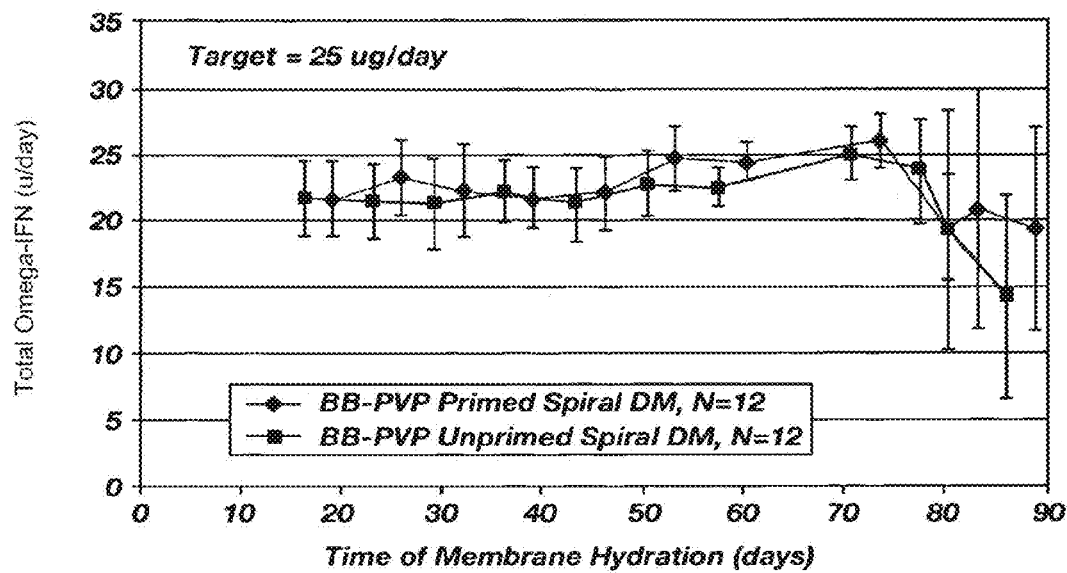
FIGS. 6 and 7 illustrate the average total omega-IFN released and the average percentage of soluble omega-IFN released, respectively, from a suspension vehicle that includes benzyl benzoate and PVP.
Figure 7:
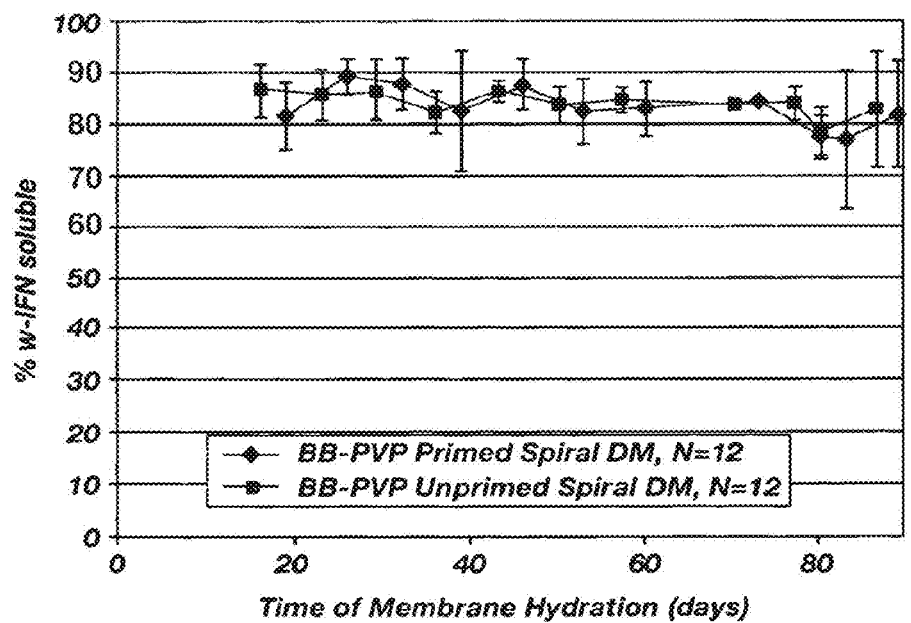

As shown in FIGS. 6 and 7, good in vitro release performance was observed with the benzyl benzoate/PVP suspension vehicle when the suspension vehicle contacted citrate buffer at 37° C. In addition, at day 89, all of the systems had intact membranes. The average total omega-IFN released was also near the target (25 μg/day) through 70 days.

Example 2

In Vivo and In Vitro Testing of Suspension Formulations Using a Straight Diffusion Moderator Four suspension formulations were tested under in vivo conditions over 90 days in rats to determine stability and in vivo release of the omega-IFN. The suspension formulations included omega-IFN as the active agent, PVP or dioleoylphosphocholine (DOPC) as the thickening agent, and lauryl alcohol (LA), benzyl benzoate, benzyl alcohol, or Vitamin E as the solvent. This experiment was designed to concentrate on the suspension formulations and used a straight polyetheretherketone (PEEK) diffusion moderator having a 0.25 mm diameter and a 15 mm length to minimize water ingress. During the experiment, efforts were made to minimize the moisture levels to which the suspension formulation was exposed. The suspension formulations were tested to determine omega-IFN release in vivo from the DUROS® systems at t=5, 9, and 13 days; failure rates (system integrity) of in vivo systems at 45 days (n=3) and 90 days (n=20) after implantation; stability assessment at 4° C. for 3, 6, and 12 months and 40° for 1, 2, 3, and 6 months; and in vitro release rate pumping into the air. The materials used in this experiment are shown in Table 3.

TABLE 3

Materials Used in the Studies

| Material |
|---|
| Omega-IFN |
| Sucrose |

TABLE 3-continued

Materials Used in the Studies

Methionine
Citrate buffer
Povidone 17PF (cleaned)
Lauryl Alcohol
Benzyl Benzoate
Benzyl Alcohol
DOPC
Vitamin E
DUROS ® Implants C-FLEX ® Piston
Fluoroelastomer Piston
DUROS ® Osmotic Tablet
Tecophilic HP-60D-33
DUROS ® Membrane
Titanium Reservoir (Gen 3) with colored band
Polyethylene Glycol 400
Silicone Fluid, MDM 350
Straight PEEK DM (0.25 × 15 mm)

The DUROS® implants used a 150 microliter Gen 3 titanium reservoir with a colored band (drawing no. 28503) fitted with clear Tecophilic HP-60D-33 membranes annealed for 7 days at 65° C.

Each of the suspension vehicles was prepared in a 60 g lot. To minimize residual moisture levels, lyophilized PVP (Povidone) was used. The moisture content of the PVP was measured before preparing the suspension vehicles. The PVP-based suspension vehicles were prepared using a Lightnin Overhead Mixer fitted with a spatula blade for the stirring paddle. The DOPC-based vehicle was prepared on a Keynes mixer. The suspension vehicles were visually inspected for particulates before proceeding. The suspension vehicles were also inspected for phase separation under the microscope at 40° C., 5° C., 0° C., and −5° C. A summary of the compositions of the suspension vehicles is presented in Table 4.

The omega-IFN was prepared as described in Example 1, except that the final target composition of the omega-IFN particles was 1:2:1:2.15 (omega-IFN:sucrose:methionine:citrate). Each suspension formulation had a target particle leading of approximately 10% (w/w). The incorporation of the omega-IFN particles into the suspension vehicle was conducted to a Scott Turbon Mixer in 25 g lots. Following deaeration, the samples were filled in 10 ml syringes and sealed in polyethylene and polyfoil pouches. Samples of the suspension formulations were stored refrigerated until filling.

The subassemblies were prepared as described in Example 1. The subassemblies and diffusion moderators for the systems were sterilized by gamma irradiation. The subassemblies were passed into and out of the drybox without subjecting the systems to purging to avoid the implants experiencing a reduced pressure environment. The subassemblies were filled with the suspension formation in the drybox using a heated syringe pump. The systems were then placed into labeled vials with their membrane side down and stoppered, but not crimped. The systems were removed from the drybox and fitted with a straight PEEK diffusion moderator with channel dimensions of 0.25 nm×15 mm. The vials were opened just prior to diffusion moderator insertion. The vials were then restoppered and brought back into the drybox in batches to ensure that the exposure time outside the drybox did not exceed 30 minutes. Each system was equilibrated unstoppered in the drybox for 30 minutes before being restoppered and crimped. The vials were then taken out of the drybox and the air bubbles in each system were assessed using X-rays. Ten systems and diffusion moderators were weighed pre- and post-filling, as well as three systems filled with silicone medical fluid. This data was used to assess the amount of air in each system. Systems were built for in vivo studies and stability. Three systems were exposed to the ambient environment for 30 minutes to quantify moisture uptake.

Each of the systems was characterized as indicated in Table 5. The homogeneity of each of the system samples was tested by monitoring the content of the omega-IFN at the beginning, middle, and end of the batch in replicates of three. This data was also used as the t=0 stability data point.

TABLE 5

Characterization Testing of Systems

| Tests | Sampling quantity and format per suspension formulation |
|---|---|
| In Vivo | 29 Implants |
| Protein Content Assay (homogeneity + stability) | 3 × 0.2 g (beginning) in vials (t = 0 homogeneity) |
| Protein Content Assay (homogeneity + stability) | 3 × 0.2 g (middle) in vials (t = 0 homogeneity) |
| Protein Content Assay (homogeneity + stability) | 3 × 0.2 g (end) in vials (t = 0 homogeneity) |
| Protein Content Assay (homogeneity + stability) | 21 Implants (stability n = 3, 7 conditions) |
| Bioburden | 3 Implants |
| Endotoxin | 1 Implant |
| X-ray | All |
| Viscosity | 1 ml |

TABLE 4

Target Compositions of Suspension Formulations

| | Suspension Vehicle Composition | | | | Drug Particle Composition | | | |
|---|---|---|---|---|---|---|---|---|
| Formulation | Solvent | Content (% w/w) | Agent | Content (% w/w) | Sucrose (% w/w) | Methionine (% w/w) | Citrate (% w/w) | ω-IFN (% w/w) |
| PDP7-200-1 | LA | 40.5 | PVP | 49.5 | 3.3% | 1.6% | 3.5% | 1.6% |
| PDP7-200-2 | BB | 44.1 | PVP | 45.9 | 3.3% | 1.6% | 3.5% | 1.6% |
| PDP7-200-3 | BA | 35.1 | PVP | 54.9 | 3.3% | 1.6% | 3.5% | 1.6% |
| PDP7-200-4 | Vit. E | 43.2 | DOPC | 46.8 | 3.3% | 1.6% | 3.5% | 1.6% |

TABLE 5-continued

Characterization Testing of Systems

| Tests | Sampling quantity and format per suspension formulation |
|---|---|
| Density | 10 systems (these systems can be also used for stability) |
| Moisture (30 min exposure) | 3 systems (no DM insertion required. Fill from beginning of the syringe.) |
| Moisture of batch | 0.3 g (vial) t = 0 |
| Moisture (stability) | Extra in vivo implants over 25 will be used for moisture stability studies. |

A more detailed summary of the stability sampling is provided in Table 6.

TABLE 6

Summary of Stability Samples

| Sample | Number of Samples | | | | | | |
|---|---|---|---|---|---|---|---|
| Sample | 5° C. (Temperature) | | | 40° C. (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0.05 g | 0.05 g | 0.05 g | 0.05 g | 0.05 g | 0.05 g | 0.05 g |
| 1 | 3 sys. | 3 sys. | 3 sys. | 3 sys. | 3 sys. | 3 sys. | 3 sys. |
| 2 | 3 sys. | 3 sys. | 3 sys. | 3 sys. | 3 sys. | 3 sys. | 3 sys. |
| 3 | 3 sys. | 3 sys. | 3 sys. | 3 sys. | 3 sys. | 3 sys. | 3 sys. |
| 4 | 3 sys. | 3 sys. | 3 sys. | 3 sys. | 3 sys. | 3 sys. | 3 sys. |

Figure 8:
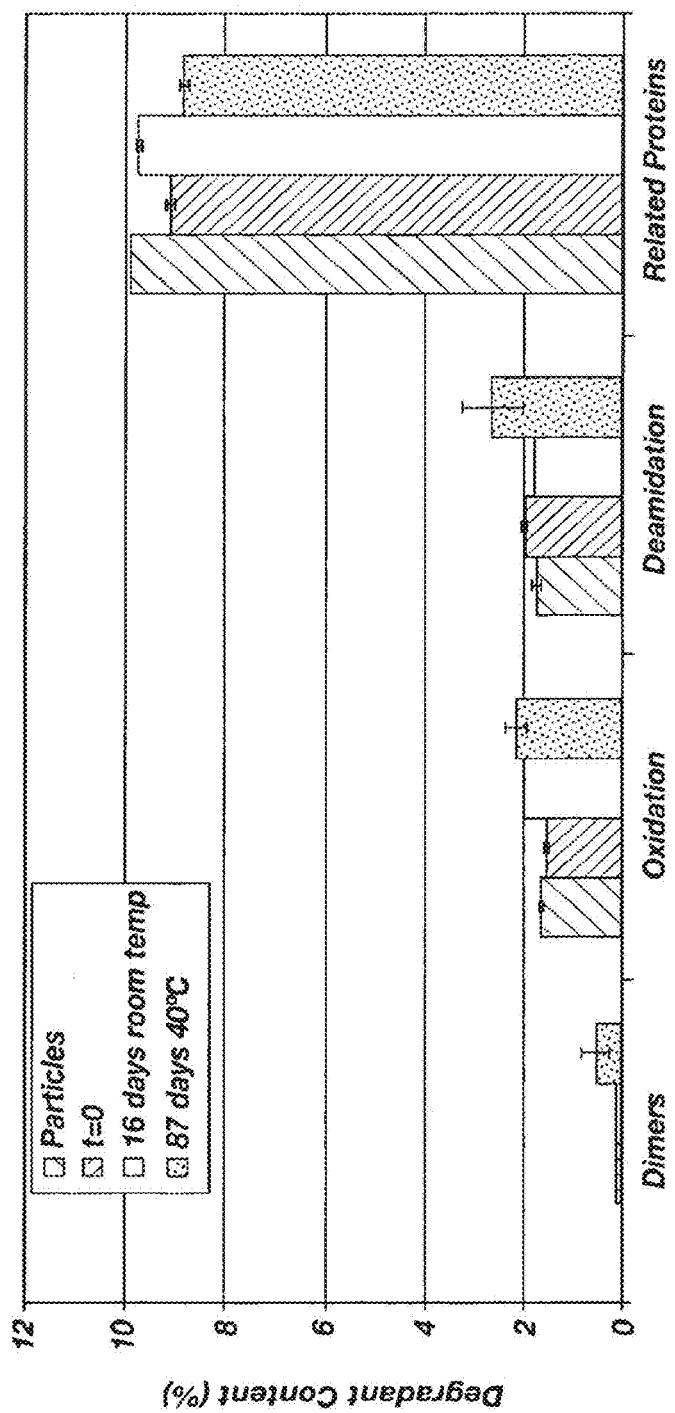
FIG. 8 illustrates the stability (dimerization, oxidation, deamidation, and related proteins) of omega-IFN in a suspension vehicle that includes benzyl benzoate and PVP.

These additional systems were sampled for stability testing of omega-IFN in suspension across all formulations. Stability test systems were sealed in glass vials under nitrogen. Stability testing for omega-IFN in each suspension formulation was performed at 1, 2, 3, and 6 months at 40° C. and at 3, 6, and 12 months at 3° C. As a control, samples of omega-IFN particles were sealed in glass vials under nitrogen and assayed at 1, 2, 3 and 6 months at 40° C. and at 3, 6, and 12 months at 5° C. These stability samples were assayed for each time temperature. Extra samples were packaged and incorporated in the stability plan as moisture studies. The stability of omega-IFN in the suspension vehicle that includes benzyl benzoate and PVP is shown in FIG. 8.

Figure 9:
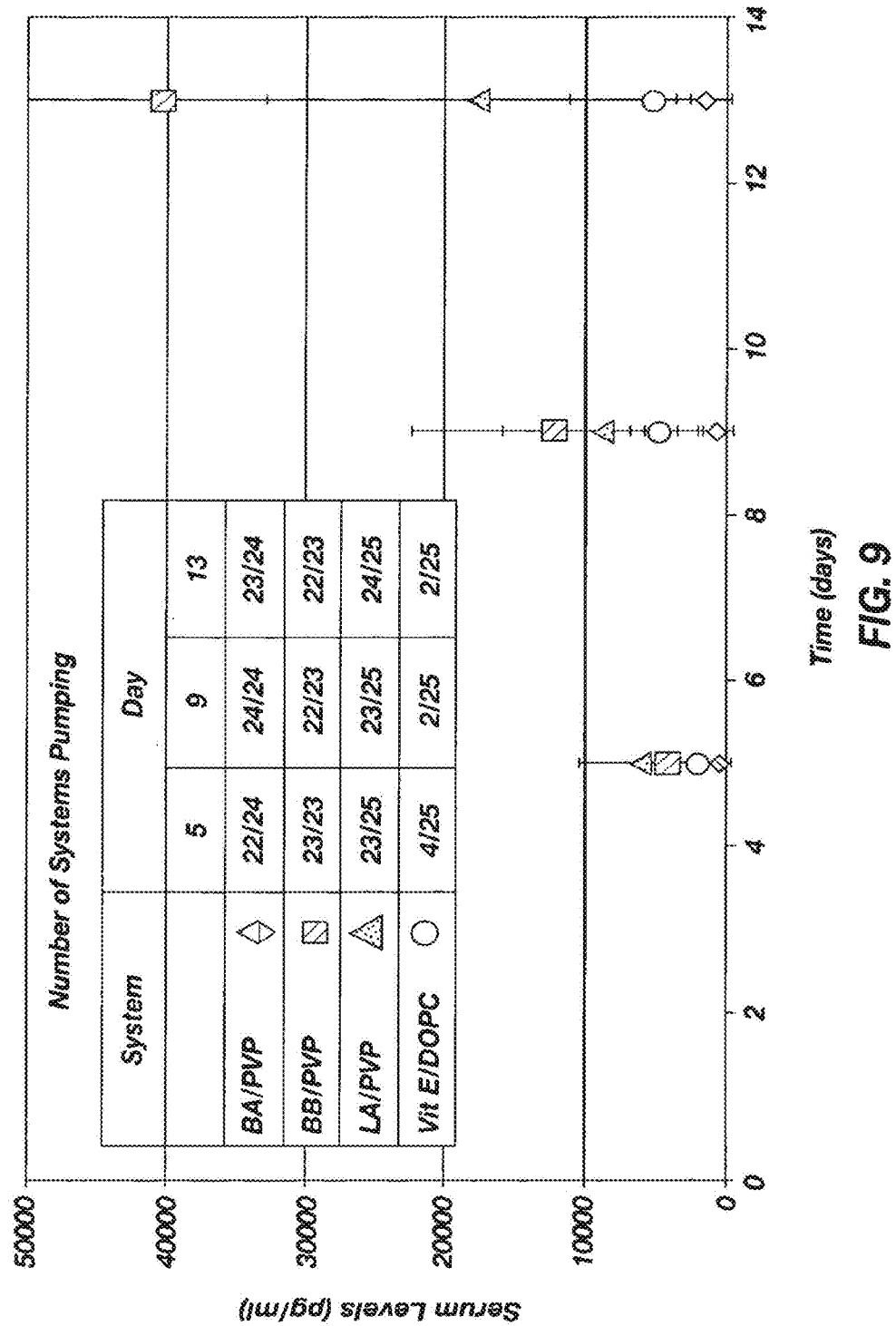
FIG. 9 is a graph illustrating the in vivo release of omega-IFN in rats.
Figure 10:
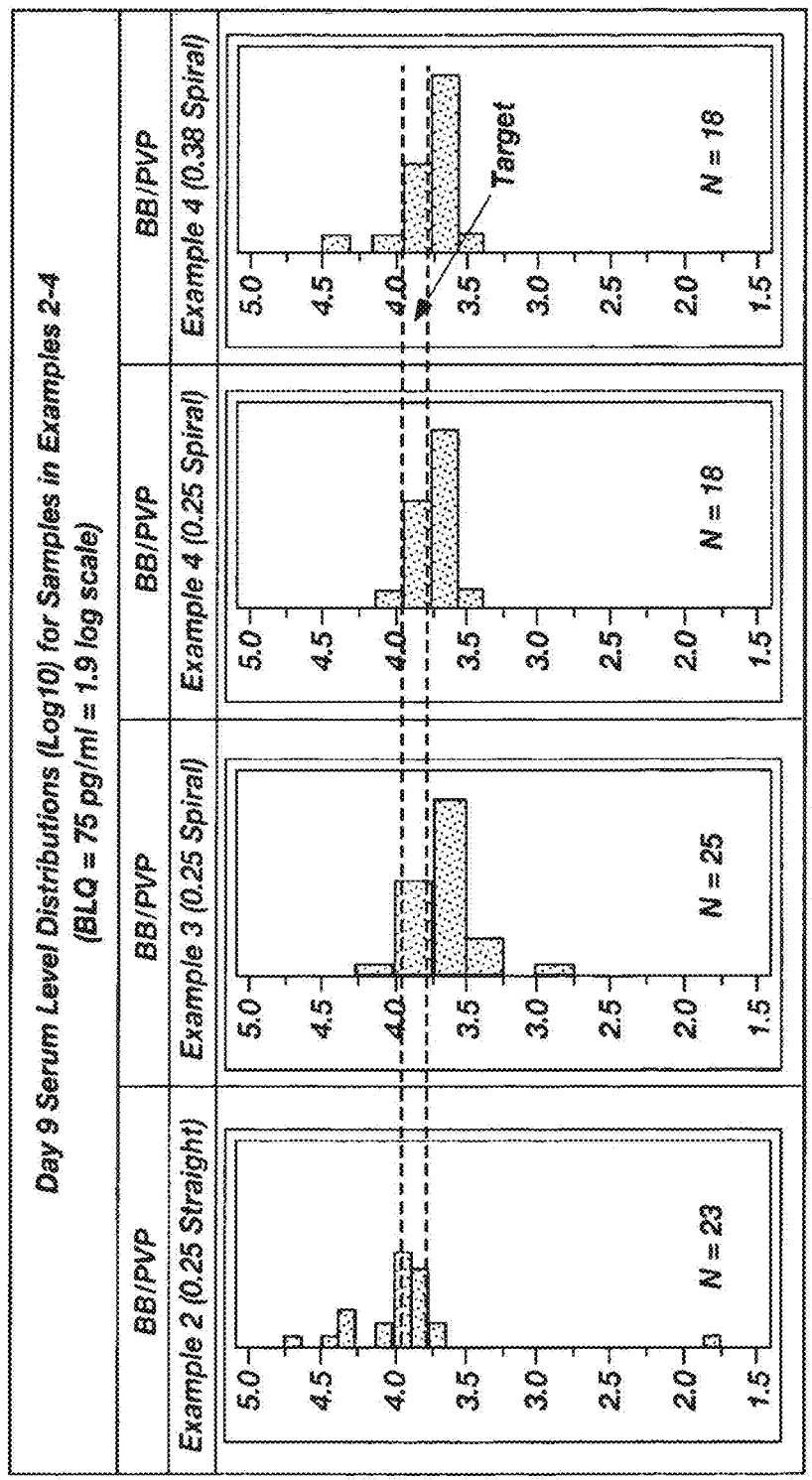
FIG. 10 shows the serum level distributions of omega-IFN nine days after implantation. In the figure, dashed lines represent log of 4000-6000 pg/ml nominal targets.

The in vivo testing of each suspension formulation was conducted by subcutaneously implanting the systems into Fischer rats. Twenty-three systems were unplanted unprimed while two systems were primed for approximately seven days prior to implantation. After implantation (t=0), blood samples were drawn and omega-IFN was assayed on day 5, 9, and 13 for each suspension formulation. Protein serum levels at days 5, 9, and 13 after implantation are shown in FIG. 9. Protein serum levels 9 days after implantation are shown in FIG. 10. FIG. 10 further include protein serum levels of samples described in Examples 3 and 4. As shown in FIG. 10, the serum levels of the omega-IFN are within target ranges. Three systems were explained at day 45 to assess system integrity. The remaining systems were explained at day 90, and all systems were intact indicating the implants performed in the planned manner. Twenty rats were required to detect approximately 30% difference. After explantation, systems/animals were tested for membrane expulsion, X-ray for piston position (final explantation only), residual protein assay, microscopic implantation site evaluation, clinical pathology (excise tissue and selected organs from all animals), implantation site histology at the DM, and assessment of capsule formation at the titanium, polyurethane, and PEEK contacting areas.

Example 3

In Vivo and In Vitro Testing of Suspension Formulations Using a Spiral Diffusion Moderator The suspension formulations described in Example 2 were investigated for system integrity and in vivo release of omega-IFN. This experiment differed from that described in Example 2 in that this experiment was focused on the ability of the suspension formulations to both release measurable omega-IFN in vivo as well as maintain system integrity using a two-piece, spiral PEEK-on-PEEK diffusion moderator with a 0.25 mm diameter and a 15 mm length. The suspension formulations were tested to determine: omega-IFN release in vivo from DUROS® systems after 2, 6, 9, and 13 days of in vivo operation (n=25), failure rates (system integrity) of in vivo systems at 29 days (n=3), 61 days (n=3), and 90 days (n=19) after implantation, the stability of omega-IFN in the suspension formulations over several months at 5° C. and 40° C., and in vitro release rate pumping into air and aqueous media. The materials used in this experiment are shown in Table 7.

TABLE 7

Materials Used in the Studies

Omega-IFN

Sucrose
Methionine
Citric Acid Monohydrate
Sodium Citrate
Povidone 17PF (cleaned)
Lauryl Alcohol
Benzyl Benzoate
Benzyl Alcohol
DOPC
Vitamin E
DUROS ® Implants C-FLEX ® Piston
Fluoroelastomer Piston
DUROS ® Osmotic Tablet
Tecophilic HP-60D-33
DUROS ® Membrane
Titanium Reservoir (Gen 3) with colored band
Polyethylene Glycol 400
Silicone Fluid, MDM 350
Spiral PEEK-on-PEEK DM (0.25 × 15 mm)

The suspension vehicles having the compositions shown in Table 8 were prepared as described in Example 2.

TABLE 8

Summary of Suspension Vehicle Composition (No omega-IFN)

| Vehicle | Solvent | Solvent Composition (% w/w) | Structuring Agent | Agent Composition (% w/w) | Nominal Viscosity Poise |
|---|---|---|---|---|---|
| 1 | Benzyl Alcohol (BA) | 39 | PVP | 61 | 15,000 |
| 2 | Benzyl Benzoate (BB) | 49 | PVP | 51 | 15,000 |
| 3 | Lauryl Alcohol (LA) | 45 | PVP | 55 | 15,000 |
| 4 | Vitamin E | 52 | DOPC | 48 | 10,000-60,000 |

The suspension formulations having the compositions shown in Table 9 were prepared as described in Example 2.

TABLE 9

Target Compositions of Suspension Formulations

| | | Vehicle Composition (90%) | | | Drug Particle Composition (10%) | | | |
|---|---|---|---|---|---|---|---|---|
| Formulation | Solvent | Content (% w/w) | Agent | Content (% w/w) | Sucrose (% w/w) | Methionine (% w/w) | Citrate (% w/w) | ω-IFN (% w/w) |
| PDP7-202-1 | BA | 35.1 | PVP | 54.9 | 3.3% | 1.6% | 3.5% | 1.6% |
| PDP7-202-2 | BB | 44.1 | PVP | 45.9 | 3.3% | 1.6% | 3.5% | 1.6% |
| PDP7-202-3 | LA | 40.5 | PVP | 49.5 | 3.3% | 1.6% | 3.5% | 1.6% |
| PDP7-202-4 | Vit. E | 46.8 | DOPC | 43.2 | 3.3% | 1.6% | 3.5% | 1.6% |

The systems were assembled and filled as described in Example 2, except that spiral PEEK-on-PEEK diffusion moderators were used instead of the straight PEEK diffusion moderators of Example 2. Systems were built for in vivo, in vitro, and stability studies, with extra systems built to allow for characterization of the suspension formulation. Microbiological and humidity controls were implemented to minimize bioburden and water content in the product, as described in Table 7 above. A representative number of systems were tested for bioburden and endotoxin to assess possible microbial contamination associated with the finished implant product.

The systems were characterized as indicated in Table 10. A more detailed summary of the stability-sampling plan is provided in Table 11.

TABLE 10

Characterization Testing of Final Systems

| Tests | Sampling quantity and format per formulation |
|---|---|
| In Vivo | 27 Implants |
| Protein Content Assay (serve as stability samples as well as homogeneity samples) | BB/PVP: 24 implants |
| Protein Content Assay (serve as stability samples as well as homogeneity samples) | BA/PVP, LA/PVP, VitE/DOPC: 15 implants |
| Bioburden | 3 Implants |
| Endotoxin | 1 Implant |
| X-ray | All |
| Viscosity | 1 ml |
| Density | 2 ml (Extra suspension left in syringe) |
| Density | 10 systems (these systems also used for stability) |
| Moisture of batch | 5 Implants |

TABLE 10-continued

Characterization Testing of Final Systems

| Tests | Sampling quantity and format per formulation |
|---|---|
| Moisture (stability) | Extra in vivo implants over 25 used for monitoring the moisture of the stability samples over time. |
| In Vitro | BB/PVP: 25 implants |
| In Vitro | BA/PVP, LA/PVP, VitE/DOPC: 15 implants |

TABLE 11

Summary of Stability Samples

| Sample | Number of Implants at Each Storage Condition | | | | | | |
|---|---|---|---|---|---|---|---|
| Sample | 5° C. (Temperature) | | | 40° C. (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0.05 g | 0.05 g | 0 | 0.05 g | 0 | 0.05 g | 0 |
| BA/PVP | 3 | 3 | 0 | 3 | 0 | 3 | 0 |
| BB/PVP | 3 | 3 | 3 | 3 | 3 | 3 | 3 |
| LA/PVP | 3 | 3 | 0 | 3 | 0 | 3 | 0 |
| VitE/DOPC | 3 | 3 | 0 | 3 | 0 | 3 | 0 |

Implants used for stability testing were sealed in glass vials under nitrogen. The implants in this experiment contained different batches of the suspension formulations than those described in Example 2, so the stability of omega-IFN in the current suspension batches was also monitored. If available, extra samples were packaged and incorporated into the stability plan to monitor changes in the moisture of the stability samples over time. As a control, samples of protein particles were sealed in glass vials under nitrogen and assayed after 1 and 3 months of storage at 40° C., and after 3 and 6 months of storage at 5° C. Three stability samples were assayed for each time and temperature combination.

The in vivo portion of this study was conducted by subcutaneously implanting the systems into Fischer rats. In all groups, 25 systems were implanted. For the benzyl alcohol/PVP, benzyl benzoate PVP, and lauryl alcohol/PVP groups, 23 systems were unprimed and 2 systems were primed. For the vitamin E/DOPC group, 15 systems were unprimed and 10 were primed. The PVP-based systems and the DOPC-based systems were primed for approximately 7 and 5 days, respectively, prior to implantation.

Blood samples were drawn on days 2, 6, 9, and 13 after implantation and the blood was assayed for omega-IFN. Three systems were explained on day 29 and an additional three systems were explained on day 61. The remaining systems were explained on day 90. After explanation, systems/animals were tested for: membrane and piston integrity; piston position (via X-ray); observations of diffusion moderator track and formulation in the drug reservoir; moisture content in the drug reservoir; residual protein content and characteristics (only in systems explanted at day 90); macroscopic implantation site evaluation; clinical pathology (excised tissue and selected organs from all animals); implantation site histology at the diffusion moderator, and assessment of capsule formation at the titanium, polyurethane, and PEEK contacting areas. Protein serum levels 9 days after implantation are shown in FIG. 10. The serum levels of the omega-IFN fell within the target ranges.

The in vitro portion of this study was conducted with approximately two-thirds of the implants delivering the suspension formulation into air and approximately one-third of the implants with the diffusion moderators (DM) immersed in the appropriate aqueous buffer. Aqueous buffers were selected based on a preliminary screening of release rare media performed by Analytical Sciences. Listed in Table 12 are the group size, diffusion moderator, and aqueous medium for each of the suspension formulations. The membrane side of the implant was immersed in phosphate buffered saline at neutral pH containing 0.2% sodium azide. The implants with their diffusion moderators immersed in the aqueous medium were unprimed so that both ends of the implant were hydrated on the same day.

TABLE 12

Release Rate Experimental Plan

| | Diffusion moderators exposed to air | Diffusion moderators exposed to aqueous medium | Aqueous medium on DM side of implant |
|---|---|---|---|
| BA/PVP (Spiral DM) | 8 | 5 | Phosphate buffer, pH 7 |
| BB/PVP (Spiral DM) | 10 | 5 | Citrate buffer, pH 6 |

TABLE 12-continued

Release Rate Experimental Plan

| | Diffusion moderators exposed to air | Diffusion moderators exposed to aqueous medium | Aqueous medium on DM side of implant |
|---|---|---|---|
| BB/PVP (Spiral DM) | 10 | 0 | Citrate buffer, pH 6 |
| LA/PVP (Spiral DM) | 10 | 5 | Phosphate buffer, pH 7 |
| VitE/DOPC (Spiral DM) | 8 | 5 | Citrate buffer, pH 2 |

The systems including the straight diffusion moderators and the benzyl benzoate PVP suspension formulations were pumped to air only.

Example 4

Effect of Start-up Conditions and Diameter of the Diffusion Moderator on In Vivo and In Vitro Performance The effect of the start-up conditions (primed, unprimed) and diffusion moderator diameter on the behavior of the systems were evaluated in three suspension vehicles (BB/PVP, LA/PVP, and lauryl lactate (LL)/PVP. The experiment used a 2-piece, PEEK-on-PEEK, spiral diffusion moderator with a channel diameter of either 0.25 mm or 0.38 mm. The effect of the diffusion moderator diameter on omega-IFN serum levels and implant survival rates over a 90-day period was determined. The length of the diffusion moderator channel was 35 mm, which is longer than the 15 mm channels used in the experiments described in Examples 2 and 3. The influx of water into the drug reservoir was monitored over time to analyze the required length of the diffusion moderator channel. In addition, the in vitro release of omega-IFN into buffer was studied.

Outputs of the in vivo portion of the study included determining serum levels of omega-IFN on days 2 and 9, at two additional intermediate timepoints, and approximately on days 75-90; failure rates (membrane integrity) of in vivo systems at 13 days (n=2) and 90 days (n=7) after implantation; and water influx into the drug reservoir of the implant at 13 days (n=2) and 90 days (n=7) after implantation. The groups used in the in vivo portion of the study are shown in Table 13.

TABLE 13

Description of the Groups Planned for the In Vivo portion of the Study Description

| Group | Formulation | DM Inner Diameter | DM Channel Length | Priming | Total N/group |
|---|---|---|---|---|---|
| 1 | BB/PVP | 0.25 mm | 35 mm (2 piece) | Yes | 9 |
| 2 | BB/PVP | 0.25 mm | 35 mm (2 piece) | No | 9 |
| 3 | BB/PVP | 0.38 mm | 35 mm (2 piece) | Yes | 9 |
| 4 | BB/PVP | 0.38 mm | 35 mm (2 piece) | No | 9 |
| 5 | LA/PVP | 0.25 mm | 35 mm (2 piece) | Yes | 9 |
| 6 | LA/PVP | 0.25 mm | 35 mm (2 piece) | No | 9 |
| 7 | LA/PVP | 0.38 mm | 35 mm (2 piece) | Yes | 9 |
| 8 | LA/PVP | 0.38 mm | 35 mm (2 piece) | No | 9 |
| 9 | LL/PVP | 0.25 mm | 35 mm (2 piece) | Yes | 9 |
| 10 | LL/PVP | 0.25 mm | 35 mm (2 piece) | No | 9 |
| 11 | LL/PVP | 0.38 mm | 35 mm (2 piece) | Yes | 9 |
| 12 | LL/PVP | 0.38 mm | 35 mm (2 piece) | No | 9 |

The materials used in this experiment are shown in Table 14.

TABLE 14

Materials Used in the Studies

Drug Particles

Omega-IFN
Sucrose
Methionine
Citric Acid Monohydrate
Sodium Citrate
Povidone 17PF (cleaned)
Lauryl Alcohol (Spectrum Chemical)
Benzyl Benzoate (Tessenderlo)
Lauryl Lactate (Chemic Laboratories)
DUROS ® Implants C-FLEX ® Piston
Fluoroelastomer Piston
Hydrosil Coating
DUROS ® Osmotic Tablet

TABLE 14-continued

Materials Used in the Studies

Tecophilic HP-60D-33
DUROS ® Membrane (clear)
Titanium Reservoir (Gen 3) with colored band
Polyethylene Glycol 400
Silicone Fluid, MDM 350
Spiral PEEK-on-PEEK DM (0.25 × 35 mm)
Spiral PEEK-on-PEEK DM (0.38 × 35 mm)
Spiral PEEK-on-PEEK DM (0.25 × 15 mm)

The formulations of the omega-IFN suspended in various vehicles were tested for stability, in vivo release, and in vitro release. The omega-IFN was prepared as described in Example 2. This study used 150 microliter Gen 3 titanium reservoirs with color band fitted with clear Tecophilic HP-60D-33 membranes annealed for 7 days at 65° C. in a low humidity forced air oven. Three suspension vehicles were prepared and tested: benzyl benzoate/PVP, lauryl alcohol/PVP, and lauryl lactate/PVP. A summary of the suspension vehicle compositions is presented in Table 15.

TABLE 15

Suspension Vehicle Compositions

| | Solvent | | Viscosity Enhancer | |
|---|---|---|---|---|
| Vehicle | Solvent | Composition (% w/w) | Agent | Composition (% w/w) |
| 1 | Benzyl Benzoate | 49 | PVP | 51 |
| 2 | Lauryl Alcohol | 45 | PVP | 55 |
| 3 | Lauryl Lactate | 50 | PVP | 50 |

The suspension vehicles were prepared in 60 g lots. To minimize residual moisture levels in the polymeric based formulations, lyophilized PVP was used. The methionine and moisture content were measured in the lyophilized PVP before preparing the suspension vehicles. The suspension vehicles were prepared using the Lightnin Overhead Mixer fitted with a spatula blade for the stirring paddle and then visually inspected for particulates before proceeding. If necessary, the suspension vehicle was centrifuged at 4,000 rpm at 65° C. for 1 hour to remove any particles. The viscosity of the suspension vehicles was measured.

Target compositions of the suspension formulations are shown in Table 16.

TABLE 16

Target Compositions of Suspension Formulations

| | | Vehicle Composition (90%) | | | Drug Particle Composition (10%) | | | |
|---|---|---|---|---|---|---|---|---|
| Formulation | Solvent | Content (% w/w) | Agent | Content (% w/w) | Sucrose (% w/w) | Methionine (% w/w) | Citrate (% w/w) | ω-IFN (% w/w) |
| PDP7-203-1 | BB | 44.1 | PVP | 45.9 | 3.3% | 1.6% | 3.5% | 1.6% |
| PDP7-203-2 | LA | 40.5 | PVP | 49.5 | 3.3% | 1.6% | 3.5% | 1.6% |
| PDP7-203-3 | LL | 45.0 | PVP | 45.0 | 3.3% | 1.6% | 3.5% | 1.6% |

Each suspension formulation had a target particle loading of approximately 10% (w/w). The omega-IFN was incorporated into the suspension vehicle by hand using a metal spatula with the suspension vehicle warmed on a hotplate. The suspension formulations were filled in 10 mL syringes, deaerated under vacuum, and sealed in polyfoil pouches. The syringes were stored at room temperature in a drybox until filling into subassemblies.

The subassemblies and diffusion moderators were prepared as described in Example 3. To insert the diffusion moderators for the LL/PVP suspension formulations, the systems were placed into labeled vials membrane side down and stoppered but not crimped. The systems were removed from the drybox and fitted with spiral PEEK-on-PEEK diffusion moderators with channel dimensions of either 0.25 nm×35 mm or 0.38 mm×35 mm. The vials were opened just prior to insertion of the diffusion moderators. The vials were then restoppered and brought back into the drybox in batches to ensure that the exposure time outside the drybox did not exceed 30 minutes. Each system was equilibrated 30 minutes in the drybox to unstoppered vials before being restoppered and crimpled.

To insert the diffusion moderators for the BB/PVP and LA/PVP suspension formulations, the filled systems were placed back into the subassembly trays. After the lid was put back in place, the subassembly traps were sealed in two layers of polyfoil bags and left in the drybox until shortly before use. Packages of the subassembly trays were opened under nitrogen atmosphere inside of the isolator. Trays containing DM/DM guide assemblies were placed in tray heaters and allowed to equilibrate for at least 30 minutes prior to insertion. Diffusion moderators with 0.25 mm diameter channels were heated to 75° C. Diffusion moderators with 0.38 mm diameter channels were heated to 65° C. Each filled subassembly was cleaned on the outside with a sterile wipe, if needed, and sealed in the DM insertion nest. After the nest was pressurized, a DM guide assembly was placed over the end of the subassembly and the DM inserter was immediately activated. Diffusion moderator insertion was carried out at approximately 3 mm/minute. After DM insertion, the system was allowed to sit in the nest for approximately 15 seconds and the end of the system was wiped with a sterile wipe. Systems were transferred from the nest to vials. After finishing a rack of 24 vials, vials were stoppered and crimp sealed in the isolator.

The final systems were characterized as indicated in Table 17.

TABLE 17

Characterization Testing of Final Systems

| Tests | Sampling quantity and format per formulation |
|---|---|
| In Vivo | 40 Implants |
| Protein Stability (also served as homogeneity samples) | BB/PVP: 9 implants |
| Protein Stability (also served as homogeneity samples) | LA/PVP: 21 implants |
| Protein Stability (also served as homogeneity samples) | LL/PVP: 21 implants |
| Bioburden | 3 Implants |
| Endotoxin | 1 Implant |
| X-ray | All |
| N-Ray | 24 implants (in vitro systems) |
| Viscosity | 1 ml (If extra suspension remains in the syringes) |
| Density | 2 ml (If extra suspension remains in the syringes) |
| Moisture of batch at t = 0 | 4 implants |
| Moisture | Extra systems will be used for monitoring the moisture of the implants over time. |
| In Vitro | BB/PVP: 24 implants |
| In Vitro | LA/PVP: 30 implants |
| In Vitro | LL/PVP: 24 implants |

A more detailed summary of the stability-sampling plan is given in Table 18.

TABLE 18

Summary of Stability Samples

| Sample | Number of Implants at Each Storage Condition (in addition to t = 0) | | | | | | |
|---|---|---|---|---|---|---|---|
| Sample | 5° C. (Temperature) | | | 40° C. (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0 | 0 | 0 | 0.05 g | 0 | 0.05 g | 0 |
| BB/PVP | 0 | 0 | 0 | 3 | 0 | 3 | 0 |
| LA/PVP | 0 | 3 | 3 | 3 | 3 | 3 | 3 |
| LL/PVP | 0 | 3 | 3 | 3 | 3 | 3 | 3 |

Implants used for stability testing were sealed in glass vials under nitrogen. The stability of the omega-IFN in the BB/PVP suspension vehicle was tested in previous experiments; therefore, a smaller stability schedule was tested in the current experiment. A larger stability study was conducted for the LA/PVP and the LL/PVP suspension formulations since new sources of solvents were used in the present study. If available, extra samples were packaged and incorporated into the stability plan to monitor changes in the moisture of the stability samples over time. As a control, samples of protein particles were sealed in glass vials under nitrogen and assayed at t=0 and after 1 and 3 months of storage at 40° C. These stability samples were assayed for each time and temperature combination planned.

The in vivo portion of this study was conducted by subcutaneously implanting the systems into Fischer rats. In each of the 12 groups outlined in Table 19, nine systems were implanted. In the groups that were primed, the length of priming was 4-5 days.

TABLE 19

Description of Groups Planned for the In Vivo Portion of the Study Description

| Group | Formulation | DM Inner Diameter | DM Channel Length | Priming | Total N/group |
|---|---|---|---|---|---|
| 1 | BB/PVP | 0.25 mm | 35 mm (2 piece) | Yes | 9 |
| 2 | BB/PVP | 0.25 mm | 35 mm (2 piece) | No | 9 |
| 3 | BB/PVP | 0.38 mm | 35 mm (2 piece) | Yes | 9 |
| 4 | BB/PVP | 0.38 mm | 35 mm (2 piece) | No | 9 |
| 5 | LA/PVP | 0.25 mm | 35 mm (2 piece) | Yes | 9 |
| 6 | LA/PVP | 0.25 mm | 35 mm (2 piece) | No | 9 |
| 7 | LA/PVP | 0.38 mm | 35 mm (2 piece) | Yes | 9 |
| 8 | LA/PVP | 0.38 mm | 35 mm (2 piece) | No | 9 |
| 9 | LL/PVP | 0.25 mm | 35 mm (2 piece) | Yes | 9 |
| 10 | LL/PVP | 0.25 mm | 35 mm (2 piece) | No | 9 |
| 11 | LL/PVP | 0.38 mm | 35 mm (2 piece) | Yes | 9 |
| 12 | LL/PVP | 0.38 mm | 35 mm (2 piece) | No | 9 |

Blood samples were drawn on days 2 and 9 after implantation, and the blood was assayed for omega-IFN. Two systems were explanted on day 13 and the remaining systems were explanted at day 90. After explantation, systems/animals were tested for membrane and piston integrity, X-ray for piston position, observations of DM track and formulation in the drug reservoir, moisture content in the drug reservoir, residual protein content and characteristics (only in systems explanted at day 90), macroscopic implantation site evaluation, clinical pathology (excise tissue and selected organs from all animals), implantation site histology at the DM, and assessment of capsule formation at the titanium, polyurethane, and PEEK, contacting areas. Protein serum levels that were measured 9 days after implantation as shown in FIG. 10. The serum levels of the omega-IFN fell within the target ranges.

In the in vitro portion of this experiment, half of the implants were primed and the remaining half of the implants had the diffusion moderator and membrane immersed in aqueous buffer on the same day (unprimed). The release rate medium was determined to be an appropriate aqueous buffer. Listed in Table 20 are the group size, diffusion moderator, and start-up conditions for each of the suspension formulations.

TABLE 20

Description of Groups Planned for the In Vitro Portion of the Study Description

| Group | Formulation | DM Inner Diameter | DM Channel Length | Start-up conditions | Total N/group |
|---|---|---|---|---|---|
| 1 | BB/PVP | 0.25 mm | 35 mm (2 piece) | Primed | 6 |
| 2 | BB/PVP | 0.25 mm | 35 mm (2 piece) | Unprimed | 6 |
| 3 | BB/PVP | 0.38 mm | 35 mm (2 piece) | Primed | 6 |
| 4 | BB/PVP | 0.38 mm | 35 mm (2 piece) | Unprimed | 6 |
| 5 | LA/PVP | 0.25 mm | 35 mm (2 piece) | Primed | 6 |
| 6 | LA/PVP | 0.25 mm | 35 mm (2 piece) | Unprimed | 6 |
| 7 | LA/PVP | 0.38 mm | 35 mm (2 piece) | Primed | 6 |
| 8 | LA/PVP | 0.38 mm | 35 mm (2 piece) | Unprimed | 6 |
| 9 | LL/PVP | 0.25 mm | 35 mm (2 piece) | Primed | 6 |
| 10 | LL/PVP | 0.25 mm | 35 mm (2 piece) | Unprimed | 6 |
| 11 | LL/PVP | 0.38 mm | 35 mm (2 piece) | Primed | 6 |
| 12 | LL/PVP | 0.38 mm | 35 mm (2 piece) | Unprimed | 6 |
| 13 | LA/PVP | 0.25 mm | 15 mm (2 piece) | Primed | 6 |

The membrane side of the implant was immersed in phosphate buffered saline at neutral pH containing 0.2% sodium azide. Group 13 was included as a control group.

The 72 systems in groups 1 through 12 were sent for N-ray imaging prior to testing in vitro to provide a greater level of detail about the systems than can be provided by X-ray due to the superior resolution of the contents of the implant when N-ray is performed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A stable, nonaqueous suspension formulation, comprising:
    a particle formulation comprising an active agent and at least one excipient, wherein:
        the active agent comprises at least one of a peptide, a polypeptide, and a protein; and
        the at least one excipient comprises methionine; and
    a nonaqueous, single-phase vehicle consisting essentially of about 10% (w/w) to about 90% (w/w) polymer and about 90% (w/w) to about 10% (w/w) solvent, wherein:
        the polymer is at least one of a polyester, a pyrrolidone, an ester of an unsaturated alcohol, an ether of an unsaturated alcohol, and a polyoxyethylenepolyoxypropylene block copolymer;
        the solvent is at least one of lauryl alcohol, lauryl lactate, benzyl benzoate, benzyl alcohol, decanol, and ethyl hexyl lactate; and
        the vehicle has a viscosity of about 1,000 poise to about 100,000 poise.

2. The suspension formulation of claim 1, wherein the at least one excipient further comprises at least one of a buffer and a sugar.

3. The suspension formulation of claim 2, wherein the at least one excipient comprises the sugar, wherein the sugar is at least one of sucrose and dextran.

4. The suspension formulation of claim 2, wherein the at least one excipient comprises the buffer, wherein the buffer is at least one of citrate, phosphate, histidine, and succinate.

5. The suspension formulation of claim 2, wherein the at least one excipient further comprises citrate and sucrose.

6. The suspension formulation of claim 1, wherein the particle formulation is formed by at least one of lyophilization, spray-drying, and freeze-drying.

7. The suspension formulation of claim 1, wherein the particle formulation is present in the suspension formulation in a range from about 0.1% (w/w) to about 50% (w/w).

8. The suspension formulation of claim 1, wherein the particle formulation is present in the suspension formulation in a range from about 3% (w/w) to about 12% (w/w).

9. The suspension formulation of claim 1, wherein the polymer is the pyrrolidone, and the pyrrolidone is polyvinylpyrrolidone (PVP).

10. The suspension formulation of claim 1, wherein the nonaqueous, single-phase vehicle consists essentially of about 25% (w/w) to about 75% (w/w) polymer and about 75% (w/w) to about 25% (w/w) solvent.

11. The suspension formulation of claim 1, wherein the nonaqueous, single-phase vehicle consists essentially of about 40% (w/w) to about 60% (w/w) polymer and about 60% (w/w) to about 40% (w/w) solvent.

12. The suspension formulation of claim 1, wherein the nonaqueous, single-phase vehicle consists essentially of about 50% (w/w) polymer and about 50% (w/w) solvent.

13. The suspension formulation of claim 1, wherein the nonaqueous, single-phase vehicle exhibits phase separation upon contact with an aqueous environment having less than about 10% water.

14. The suspension formulation of claim 1, wherein the viscosity is about 5,000 poise to about 50,000 poise.

15. The suspension formulation of claim 1, wherein the viscosity is about 10,000 poise to about 20,000 poise.

16. The suspension formulation of claim 1, wherein the viscosity is measured at 37° C.

17. An implantable osmotic drug delivery device, comprising:
    a reservoir containing a stable, nonaqueous suspension formulation, the suspension formulation comprising:
        a particle formulation comprising an active agent and at least one excipient, wherein:
            the active agent comprises at least one of a peptide, a polypeptide, and a protein; and
            the at least one excipient comprises methionine; and
        a nonaqueous, single-phase vehicle consisting essentially of about 10% (w/w) to about 90% (w/w) polymer and about 90% (w/w) to about 10% (w/w) solvent, wherein:
            the polymer is at least one of a polyester, a pyrrolidone, an ester of an unsaturated alcohol, an ether of an unsaturated alcohol, and a polyoxyethylene-polyoxypropylene block copolymer;
            the solvent is at least one of lauryl alcohol, lauryl lactate, benzyl alcohol, benzyl benzoate, decanol, and ethyl hexyl lactate; and
            the vehicle has a viscosity of about 1,000 poise to about 100,000 poise; and
    an orifice through which at least the active agent is delivered.

18. A method of making a stable, nonaqueous suspension formulation, the method comprising:
    combining a polymer and a solvent under dry conditions to form a nonaqueous, single-phase vehicle consisting essentially of about 10% (w/w) to about 90% (w/w) polymer and about 90% (w/w) to about 10% (w/w) solvent, wherein:

the polymer is at least one of a polyester, a pyrrolidone, an ester of an unsaturated alcohol, an ether of an unsaturated alcohol, and a polyoxyethylenepolyoxypropylene block copolymer;

the solvent is at least one of lauryl alcohol, lauryl lactate, benzyl alcohol, benzyl benzoate, decanol, and ethyl hexyl lactate; and the vehicle has a viscosity of about 1,000 poise to about 100,000 poise; and adding a particle formulation comprising an active agent and at least one excipient to the vehicle to form the suspension formulation, wherein:

the active agent comprises at least one of a peptide, a polypeptide, and a protein; and the at least one excipient comprises methionine.

19. The method of claim 18, wherein a vacuum is applied during the combining to remove air bubbles from the vehicle, wherein the vacuum is about −5 Hg to about −30 Hg.

20. The method of claim 18, wherein the polymer and the solvent are combined at an elevated temperature, wherein the elevated temperature is about 40° C. to about 70° C.

* * * * *